(12) United States Patent
Kerr et al.

(10) Patent No.: US 11,319,336 B2
(45) Date of Patent: May 3, 2022

(54) SHIP INHIBITORS AND USES THEREOF

(71) Applicant: The Research Foundation For The State University Of New York, Syracuse, NY (US)

(72) Inventors: William G. Kerr, Syracuse, NY (US); John D. Chisholm, Syracuse, NY (US)

(73) Assignee: THE RESEARCH FOUNDATION FOR THE STATE UNIVERSITY OF NEW YORK

( * ) Notice: Subject to any disclaimer, the term of this patent is extended or adjusted under 35 U.S.C. 154(b) by 0 days.

(21) Appl. No.: 15/269,209

(22) Filed: Sep. 19, 2016

(65) Prior Publication Data

US 2017/0051006 A1    Feb. 23, 2017

Related U.S. Application Data

(62) Division of application No. 13/640,162, filed as application No. PCT/US2011/031930 on Apr. 11, 2011, now Pat. No. 9,447,139.

(60) Provisional application No. 61/322,378, filed on Apr. 9, 2010.

(51) Int. Cl.
*C07J 41/00* (2006.01)
*C07J 1/00* (2006.01)

(52) U.S. Cl.
CPC ......... *C07J 1/0007* (2013.01); *C07J 41/0005* (2013.01); *C07J 41/0011* (2013.01)

(58) Field of Classification Search
CPC ... C07J 1/0007; C07J 41/0005; C07J 41/0011
See application file for complete search history.

(56) References Cited

U.S. PATENT DOCUMENTS

| | | | |
|---|---|---|---|
| 9,006,221 B2 * | 4/2015 | Kerr | A61K 31/575 514/169 |
| 2005/0004382 A1 | 1/2005 | Grondahl et al. | |
| 2008/0255076 A1 | 10/2008 | Braxmeier et al. | |
| 2010/0216752 A1 | 8/2010 | Bordet et al. | |
| 2012/0178725 A1 | 7/2012 | Kerr | |

FOREIGN PATENT DOCUMENTS

| | | | | |
|---|---|---|---|---|
| BE | 702699 | A | | 1/1968 |
| CS | 126 738 | B5 | | 3/1968 |
| CZ | 126738 | | | 8/1985 |
| GB | 900572 | A | | 7/1962 |
| GB | 1000410 | A | * 8/1965 | ............. C07J 41/00 |
| WO | 2004032880 | A2 | | 4/2004 |
| WO | 2008/068037 | A1 | | 6/2008 |
| WO | 2010/045199 | A2 | | 4/2010 |
| WO | 2011069118 | A1 | | 6/2011 |
| WO | 2011127465 | A2 | | 10/2011 |
| WO | 2015003003 | A1 | | 1/2015 |

OTHER PUBLICATIONS

STN Registry Database Compound 54156-22-8 (entered STN Nov. 16, 1984).*
STN Registry Database Compound 54156-38-6 (entered STN Nov. 16, 1984).*
STN Registry Database Compound 57-88-5 (entered STN Nov. 16, 1984).*
STN Registry database compound 81916-93-0 (entered STN Nov. 16, 1984) (Year: 1984).*
STN Registry database compound 20707-85-1 (entered STN Nov. 16, 1984) (Year: 1984).*
STN Registry database compound 187943-78-8 (entered STN Apr. 3, 1997) (Year: 1997).*
STN Registry database compound 557103-30-7 (entered STN Jul. 30, 2003). (Year: 2003).*
STN Registry database compound 20707-77-1 (entered STN Nov. 16, 1984) (Year: 1984).*
Ito et al. (Cancer Sci, Jan. 2003, vol. 94, pp. 3-8) (Year: 2003).*
Silver et al., "Annals of the New York Academy of Sciences" (1970), 171 (Art. 3), 838-62 CODEN: ANYAA9; ISSN: 0077-8923.*
International Search Report and Written Opinion issued in PCT/US2011/031930, dated Dec. 27, 2011.
Nikolaropoulos et al., "Formation of Acetamido-Aza-Steroids," *J. Heterocyclic Chem.*, 27:1997-1999 (1990).
Phillipps et al., "A New Series of Steroidal Antidysrhythmic Agents," *J. Steroid Biochem.*, 19(1):759-765 (1983).
Syhora et al., "Olefine-Forming Elimination of the Amido Group," *Tetrahedron Letters*, 28:2369-2376 (1965).
Extended European Search Report issued in European Patent Application No. 11766857.4, dated Jan. 17, 2014.
Cowell et al., "Bromo, chloro, and amino derivatives of 5.alpha.-androstane and 5.alpha.-estrane", Journal of the Chemical Society, Perkin Transactions 1, Chemical Society, vol. 1974, No. 13, Jan. 1, 1974, pp. 1505-1513.
Ahmad et al., "Synthesis of facial amphiphile 3,7-diamino-5.alpha.-cholestane derivatives as a molecular receptor", Bulletin of the Korean Chemical Society, vol. 30, No. 9, 2009, pp. 2101-2106.

(Continued)

*Primary Examiner* — Jared Barsky
(74) *Attorney, Agent, or Firm* — Michael Krenicky; Steven A. Wood, Jr.

(57) ABSTRACT

The present invention relates to SHIP inhibitor compounds and methods for using these compounds. In particular, the present invention discloses the following methods: (i) a method of treating graft versus host disease in a subject; (ii) a method of inhibiting a SHIP1 protein in a cell; (iii) a method of selectively inhibiting a SHIP1 protein in a cell; (iv) a method for treating or preventing graft-versus-host disease (GVHD) in a recipient of an organ or tissue transplant; (v) a method of modulating SHIP activity in a cell expressing SHIP1 or SHIP2; (vi) a method of ex vivo or in vitro treatment of transplants; (vii) a method of inhibiting tumor growth and metastasis in a subject; (viii) a method of treating a hematologic malignancy in a subject; (ix) a method of inducing apoptosis of multiple myeloma cells; (x) a method of treating multiple myeloma in a subject; (xi) a method of inhibiting the proliferation of a human breast cancer cell; and (xii) a method of treating breast cancer in a subject.

11 Claims, 8 Drawing Sheets

(56) References Cited

OTHER PUBLICATIONS

Francisco et al., "Aminoselenenylation of Alkenes: Syntheses of p-Phenylseleno Carbamates and p-Phenylseleno Cyanamides", Journal of the Chemical Society, No. 9, Jan. 1990, pp. 2417-2427.
Smith et al. "Optically active amines. 30. Application of the salicylidenimino chirality rule to aliphatic and alicyclic amines", The Journal of Organic Chemistry, vol. 47, No. 13, Jun. 1, 1982, pp. 2525-2531.
Ponsold et al., „Dartsellung und Ringoffnungsreaktionen der epimeren 2.3-Imino-cholestane, Chemische Berichte, vol. 99, No. 5, Jan. 1, 1966, pp. 1502-1508.
Yagi et al., "Synthesis of C-3 ureido steroids", The Journal of Organic Chemistry, vol. 32, No. 3, Mar. 1, 1967, pp. 713-718.
Jang et al., "Synthesis of 9-Anthryl Ethers from trans-9, 10-Dihydro-9, 10-dimethoxy-anthracene by Acid-Catalyzed Transetherification", Synthesis, vol. 2009, No. 10, Apr. 30, 2009, pp. 1703-1707.
Harwood et al., "The synthesis of 3.alpha.-/3 .beta.-cholesteryl and cholestanyl esters and esthers—an assessment of their mesogenicity", Molecular Crystals and Liquid Crystals Science and Technology. Section A. Molecular Crystals and Liquid Crystals; Proceedings of the 17$^{th}$ International Liquid Crystal Conference: Strasbourg, France, Jul. 19-24, 1998, vol. 332, Jan. 1, 1999.
Vill et al., "Liquid crystalline cholestanyl and cholesteryl ether lipids", Molecular Crystals and Liquid Crystals Science and Technology. Section A. Molecular Crystals and Liquid Crystals, vol. 250, Jan. 1, 1994, pp. 73-83.
Manhas et al., "Steroids. Part X. 1 A Convenient Synthesis of Alkyl Aryl Ethers", Journal of the Chemical Society, Perkin Transactions 1: Organic and Bio-Organic Chemistry, No. 5, Jan. 1, 1975, pp. 461-463.
Wu et al., "Organic Photochemistry. Part 94. Triethylamine-Photosensitized Reduction of a Ketone Via a Chemical Sensitization Mechanism", Journal of the American Chemical Society, vol. 114, No. 5, Feb. 1, 1992, pp. 1812-1816.
Annis et al., "Inhibitors of the Lipid Phosphatase SHIP2 Discovered by High Throughput Affinity Selection-Mass Spectrometry Screening of Combinatorial Libraries", Combinatorial Chemistry and High Throughput Screening, vol. 12, No. 8, Sep. 1, 2009, pp. 760-771.
Suwa et al., "Discovery and Functional Characterization of a Novel Small Molecule Inhibitor of the Intracellular Phosphatase, SHIP2", British Journal of Pharmacology, vol. 158, No. 3, Oct. 19, 2009, pp. 879-887.
Cannon, Chapter 19 in Burger's Medicinal Chemistry and Drug Discover, 5$^{th}$ Edition, vol. 1: Principles and Practice, Wiley-Interscience 1995, pp. 783-802, 784.
Liu et al. (Cancer Research, 2005, 65, 2269-2276).
Silver et al. (Annals of the New York Academy of Sciences, 1970, 171, 838-862).
Medline Plus (Fungal Infections; Jul. 22, 2008).
Hungria et al. (Cancer Chemotherm Pharmacol, 2004, 53, 51-60).
Li et al., Short Synthesis of Triamine Derivatives of Cholic Acid, 1999, Tetrahedron Letters, 40, 1861-1864.

* cited by examiner

3α-Amino-5α-androstane (3A5AS)

SHIP INHIBITORS AND USES THEREOF

CROSS-REFERENCE TO RELATED APPLICATIONS

This application is a divisional of U.S. application Ser. No. 13/640,162, filed Oct. 9, 2012, and published as 2013-0102577A1 on Apr. 25, 2013, which is a § 371 U.S. National Phase application of PCT application PCT/US11/31930, filed Apr. 11, 2011, and published as WO 2011/127465 on Oct. 13, 2011, and claims priority benefit of U.S. Provisional Patent Application Ser. No. 61/322,378, filed Apr. 9, 2010. The entire contents of each of the prior applications are incorporated herein by reference in their entirety.

GOVERNMENT RIGHTS STATEMENT

This invention was made with Government support under grants HL085580 and HL072523 awarded by the National Institutes of Health. The Government has certain rights in the invention.

FIELD OF THE INVENTION

The present invention relates to small molecule inhibitors of SHIP and therapeutic uses of these inhibitors.

BACKGROUND OF THE INVENTION

Src homology 2 domain-containing inositol 5-phosphatase 1 (SHIP-1 or SHIP1) is a cytosolic protein that has been found to control the intracellular level of the phosphoinositide 3-kinase product phosphotidylinositol-3,4,5-trisphosphate and function as a negative regulator of cytokine and immune receptor signaling. Using various genetic models, it has been shown that SHIP1 deficient hosts are permissive for engraftment of major histocompatibility complex (MHC) mismatched bone marrow (BM) grafts, exhibit reduced GVHD post-transplant and delayed rejection of vascularized allogeneic heart grafts (Refs. 1-5). In addition, SHIP1 deficiency profoundly increases myeloid immunoregulatory (MIR) cell numbers and their function and granulocyte numbers (Refs. 2, 4, 6-8). These studies suggest that SHIP1 could be targeted to facilitate increase granulocyte/neutrophil numbers during infection or to reduce the severity and incidence of deleterious allogeneic T cell responses in bone marrow and organ transplantation (Ref 5).

SHIP1, SHIP2 and PTEN are commonly viewed as opposing the activity of the PI3K/Akt signaling axis that promotes survival of cancer cells and tumors. However, the enzymatic activities of these inositol phosphatases are quite distinct in that the 3'-polyphosphatase activity of PTEN reverses the PI3K reaction to generate $PI(4,5)P_2$ from $PI(3,4,5)P_3$, while the 5'-poly-phosphatase activity of SHIP1/2 converts $PI(3,4,5)P_3$ to $PI(3,4)P_2$. This distinction is potentially crucial as it might enable SHIP1/2 and PTEN to have distinctly different effects on Akt signaling. The PH domain of Akt binds with greater affinity to the SHIP1/2 product $PI(3,4)P_2$ leading to more potent activation of Akt than the direct product of PI3K, $PI(3,4,5)P_3$ (Ref. 9). Thus, SHIP1, which is expressed in most blood cell malignancies, might actually contribute to their growth and survival. Consistent with this hypothesis, $PI(3,4)P_2$ levels are increased in leukemia cells (Ref 10) and increased levels of $PI(3,4)P_2$ promote the transformation and tumorigenicity of mouse embryonic fibroblasts (MEF) (Ref. 11).

To date the molecular structure of SHIP1 has not been determined and thus a rational design approach to develop SHIP1 inhibitors has not been feasible. Thus, High-Throughput Screening (HTS) tests have been used to identify compounds that can inhibit the enzymatic activity of SHIP1. However, there is a need for SHIP1 selective inhibitors that are capable of increasing granulocyte and MIR cell production in vivo and promoting apoptosis of blood cell cancers.

The present invention is directed to overcoming these and other deficiencies in the art.

SUMMARY OF THE INVENTION

In one aspect, the present invention relates to SHIP inhibitor compounds of the formula (I), and pharmaceutically acceptable salts thereof, where formula (I) is as follows:

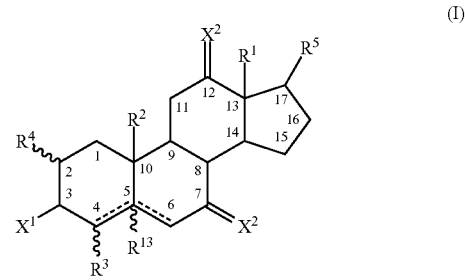

(I)

wherein the groups $R^1$, $R^2$, $R^3$, $R^4$, $R^5$, $R^{13}$, $X^1$, and $X^2$ are as hereinafter defined below.

The "SHIP inhibitor compounds" of the present invention are also referred to herein as "SHIP inhibitors," "SHIP1 inhibitors," "SHIP1 inhibitor compounds," and the like. In one embodiment, the SHIP inhibitor compounds of the present invention are selective inhibitors of SHIP1.

$R^1$ is a straight chain $C_1$-$C_4$ alkyl or $C_1$-$C_4$ haloalkyl. In one embodiment, $R^1$ is methyl.

$R^2$ is hydrogen, methyl, or halomethyl. In one embodiment, $R^2$ is methyl.

$R^3$ is hydrogen, substituted or unsubstituted amino, $C_1$-$C_4$ alkyl, $C_1$-$C_4$ haloalkyl, or $C_1$-$C_4$ alkenyl. In one embodiment, both $R^3$ and $R^{13}$ are hydrogen.

$R^4$ is hydrogen, hydroxy, substituted or unsubstituted amino, alkyl, or benzyl. In one embodiment, $R^4$ is hydrogen.

$R^5$ includes a divalent oxo atom, or two hydrogen atoms, or one hydrogen atom together with an alkyl group. In one embodiment, $R^5$ represents one hydrogen atom together with an alkyl group. In one embodiment, alkyl group is 1,5-dimethylhexyl.

$X^1$ may be selected from the group consisting of hydrogen, hydroxy, mercapto, alkoxy, aryloxy, alkylthio, and arylthio. The alkoxy, aryloxy, alkylthio, and arylthio moieties may be further substituted.

$X^1$ may also be selected from the group consisting of alkylcarbonamido, arylcarbonamido, aminocarbonamido, hydrazinocarbonamido, alkylsulfonamido, arylsulfonamido, aminosulfonamido, and hydrazinosulfonamido, all of which may be further substituted.

$X^1$ may also be selected from the group consisting of ($C_1$-$C_4$ alkyl)carbonyloxy, ($C_1$-$C_4$ alkoxy)carbonyloxy, arylcarbonyloxy, aryloxycarbonyloxy, and aminocarbonyloxy, all of which may be further substituted.

$X^1$ may further be selected from the group consisting of a substituted or unsubstituted amino and secondary and tertiary amino groups that include at least one $C_1$-$C_4$ alkyl, $C_5$-$C_6$ cycloalkyl, aryl, or heterocyclic substituent, or combinations thereof. In one embodiment, the secondary or tertiary amino group contains at least one $C_1$-$C_4$ alkyl moiety, which may be further substituted.

$X^1$ may further be an aminoalkyl group, amino($CH_2$)$_n$, where "amino" is an unsubstituted or a substituted secondary or tertiary amino as defined above, and n is an integer from 1 to 4.

$X^1$ may further represent a divalent oxygen moiety, =O, or a divalent N-hydroxyamino moiety, =NOH.

$X^1$ may further be an amino group, except when: $R^1$ and $R^2$ are each methyl; $X^2$, $R^3$, $R^4$, and $R^{13}$ are each hydrogen; and $R^5$ represents one hydrogen atom together with an alkyl group, where the alkyl group is 1, 5-dimethylhexyl alkyl group.

Each $X^2$ is independently defined to represent a divalent oxo or two hydrogen atoms. In one embodiment, each $X^2$ represents two hydrogen atoms.

In another aspect, the present invention relates to a method of treating graft versus host disease in a subject. This includes the step of administering a SHIP1 inhibitor of the present invention to a subject in need of treatment.

In a further aspect, the present invention relates to a method of inhibiting a SHIP1 protein in a cell. The method includes the step of contacting the cell containing a SHIP1 protein with a SHIP1 inhibitor of the present invention.

In yet another aspect, the present invention relates to a method of selectively inhibiting a SHIP1 protein in a cell. The method includes the step of contacting the cell containing a SHIP1 protein with a SHIP1 inhibitor of the present invention, wherein the SHIP1 inhibitor of the present invention is provided in an amount effective to inhibit SHIP1 but not to inhibit SHIP2 or PTEN.

In another aspect, the present invention relates to a method for treating or preventing graft-versus-host disease (GVHD) in a recipient of an organ or tissue transplant. The method includes the step of administering to the transplant recipient a SHIP inhibitor of the present invention in a pharmaceutically effective amount after the transplantation. In certain embodiments the step of administering the SHIP1 inhibitor is performed prior to the organ or tissue transplant.

In another aspect, the present invention relates to a method of modulating SHIP activity in a cell expressing SHIP1 or SHIP2. The method includes the step of contacting the cell with at least one SHIP inhibitor of the present invention. In a particular embodiment, the SHIP modulation is used to prevent at least one disease selected from the group consisting of autoimmune disease, graft-versus-host disease, and solid organ graft rejection, dietary-induced obesity, tumor cell growth. The modulated SHIP can be SHIP1 or SHIP2. In another embodiment, the SHIP modulation is used to prevent dietary-induced obesity. In further embodiments, the SHIP modulation can be used to modulate cell numbers and functions of cells selected from the group consisting of hematopoietic stem cells, NK cells, Treg cells, and myeloid derived suppressor cells. The Treg cells are naive FoxP3+ T cells. In still further embodiments, the SHIP modulation is used to convert naive/effector CD4+ T cells into immunoregulatory cells. In further embodiments, the SHIP modulation can be used to facilitate engraftment of cells selected from the group consisting of allogenic bone marrow stem cells, hematopoietic stem cells, pluripotent stem cells, IPS, and derivatives thereof.

In another aspect, the present invention relates to a method of ex vivo or in vitro treatment of transplants. The method can include the steps of isolating blood derived cells, bone marrow transplants, or organ transplants and contacting the isolated blood derived cells, bone marrow transplants, or organ transplants with a SHIP inhibitor of the present invention. The treatment of transplants serves to inactivate T-lymphocytes contained in the sample.

In another aspect, the present invention relates to a method of inhibiting tumor growth and metastasis in a subject. The method includes the step of administering to the subject one or more SHIP inhibitors of the present invention.

In another aspect, the present invention relates to a method of treating a hematologic malignancy in a subject. The method includes the step of administering to the subject one or more SHIP inhibitors of the present invention. The hematologic malignancy can be a leukemia, lymphoma, multiple myeloma, myelodysplastic syndrome (MDS), myeloproliferative disease (MPD) or MDS/MPD diseases. In certain embodiments the leukemia is acute lymphoblastic leukemia, acute myelogenous leukemia, chronic myelogenous leukemia, or chronic lymphocytic leukemia. In certain embodiments the lymphoma is Hodgkin's disease, small lymphocytic lymphoma, diffuse large B-cell lymphoma, follicular lymphoma, mantle cell lymphoma, hairy cell leukemia, marginal zone lymphoma, Burkitt's lymphoma, Post-transplant lymphoproliferative disorder, T-cell pro lymphocytic leukemia, B-cell prolymphocytic leukemia, Waldenstrom's macroglobulinemiallymphoplasmacytic lymphoma, orother NK- or T-cell lymphomas. In certain embodiments the myeloproliferative disease is polycythemia vera, essential thrombocytosis or myelofibrosis. In certain embodiments the MDS/MPD disease is chronic myelomonocytic leukemia, juvenile myelomonocytic leukemia, and atypical chronic myeloid leukemia.

In another aspect, the present invention relates to a method of inducing apoptosis of multiple myeloma cells. The method includes the step of contacting the cells with one or more SHIP inhibitors of the preset invention.

In another aspect, the present invention relates to a method of treating multiple myeloma in a subject. The method includes the step of administering to the subject one or more SHIP inhibitors of the present invention.

In another aspect, the present invention relates to a method of inhibiting the proliferation of a human breast cancer cell. The method includes the step of contacting the cell with one or more SHIP inhibitors of the present invention.

In another aspect, the present invention relates to a method of treating breast cancer in a subject. The method includes the step of administering to the subject one or more SHIP inhibitors of the present invention.

In another aspect, the present invention relates to a method of treating myelosuppression in a subject. This method includes the step of administering to the subject one or more SHIP1 inhibitor compound of the present invention under conditions effective to treat myelosuppression in the subject.

In another aspect, the present invention relates to a method of treating anemia in a subject. This method includes the step of administering to the subject one or more SHIP1 inhibitor compound of the present invention under conditions effective to treat anemia in the subject.

In another aspect, the present invention relates to a method of increasing platelets in a subject. This method includes the step of administering to the subject one or more SHIP1 inhibitor compound of the present invention under conditions effective to increase platelets in the subject.

In another aspect, the present invention relates to a method of aiding recovery of a subject who has undergone a bone marrow transplant. This method includes the step of administering to the subject one or more SHIP1 inhibitor compound of the present invention under conditions effective to increase production in the subject of blood cell components, thereby aiding the post-bone marrow transplant recovery of the subject. This method can be used to aid the recovery of subjects who have undergone an autologous bone marrow transplant or an allogenic bone marrow transplant. In one embodiment, this method can further include administering at least one growth factor to the subject along with the one or more SHIP1 inhibitor compound.

In another aspect, the present invention relates to a method of enhancing blood stem cell harvest from a subject. This method includes the step of administering to the subject one or more SHIP1 inhibitor compound of the present invention under conditions effective to mobilize stem cells in the subject from the bone marrow to the blood.

BRIEF DESCRIPTION OF THE DRAWINGS

FIG. 6A: Malachite Green assay for SHIP1 activity against PI(3,4,5)$P_3$ substrate in the presence of 3AC or 3A5AS. The "No SHIP" column indicates background absorbance when the assay is carried out with PIP3 substrate in the absence of recombinant SHIP1. FIG. 6B: MTT assay of C1498 leukemia growth in the presence of 3AC and 3A5AS at the indicated concentrations. FIG. 6C: Examples of MIR cell induction in 3AC- and 3A5AS-treated mice as compared to a vehicle control. FIG. 6D: Bar graphs and statistical analysis of MIR cell numbers in the indicated treatment groups (**, p<0.01; NS, not significant). [Noto bene: DRV-IV-26=3A5AS]

DETAILED DESCRIPTION OF THE INVENTION

Figure 1:
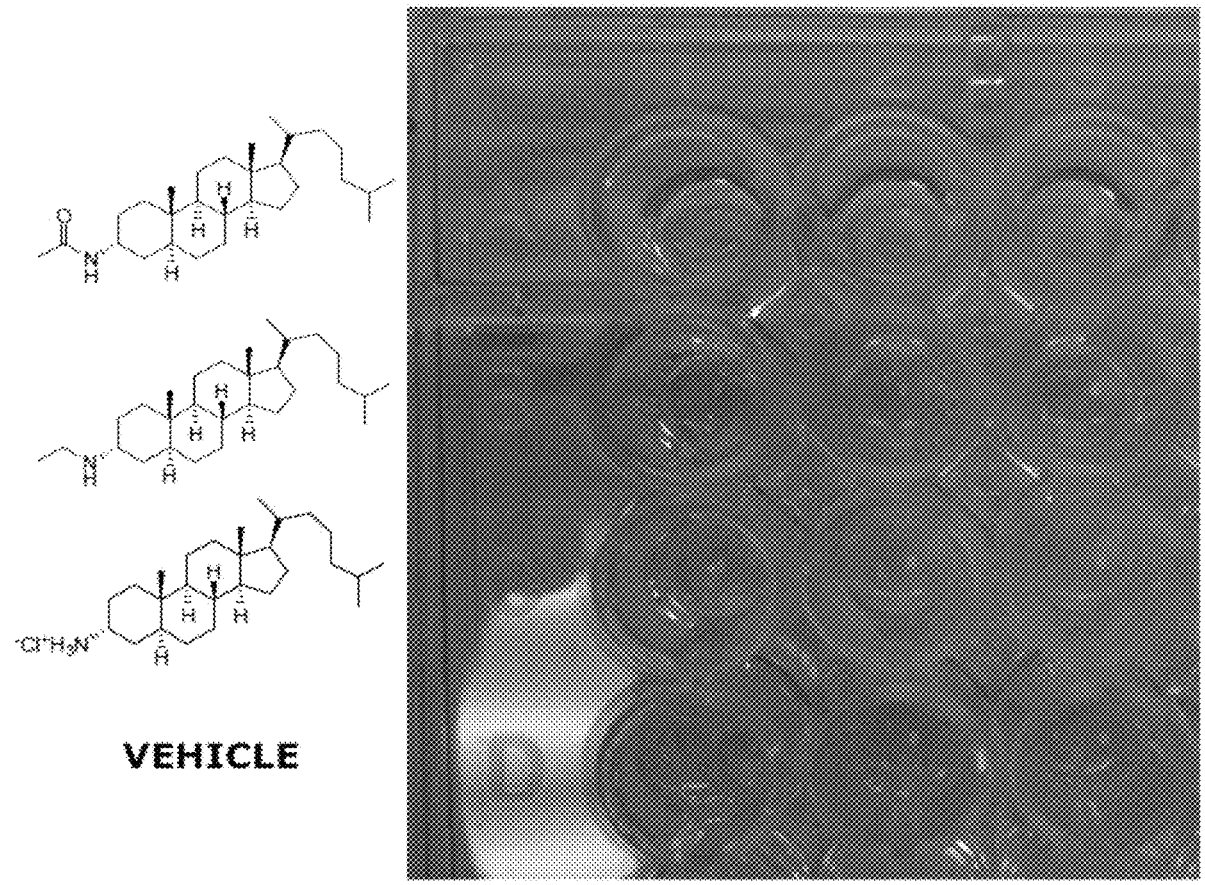
FIG. 1 shows the results of a SHIP1 malachite phosphatase assay. Lack of green color indicates inhibition for the amide and the hydrochloride, while the ethylamine is a poor inhibitor
Figure 2:
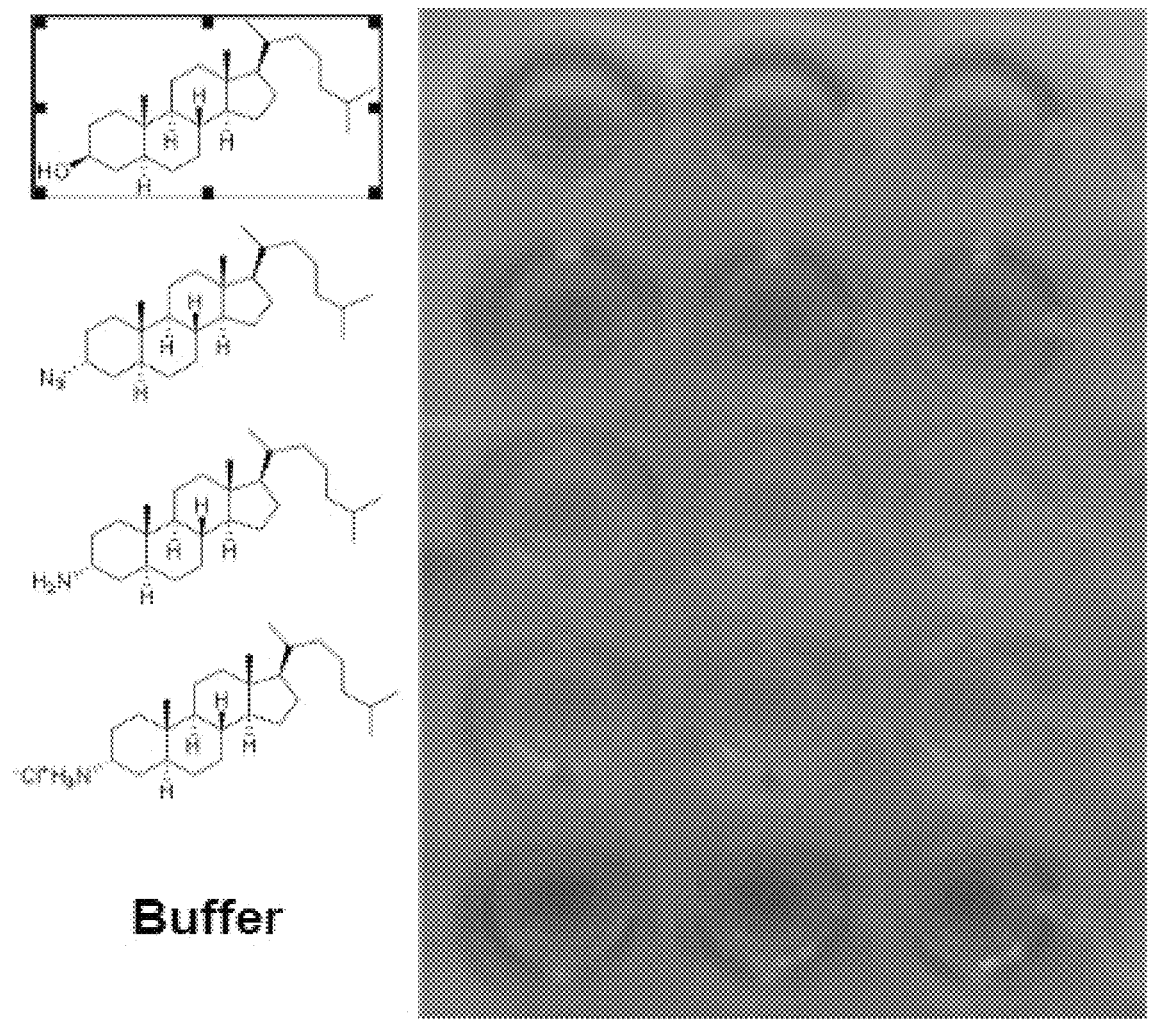
FIG. 2 shows the results of a SHIP1 malachite phosphatase assay. Lack of green color indicates inhibition.
Figure 3:
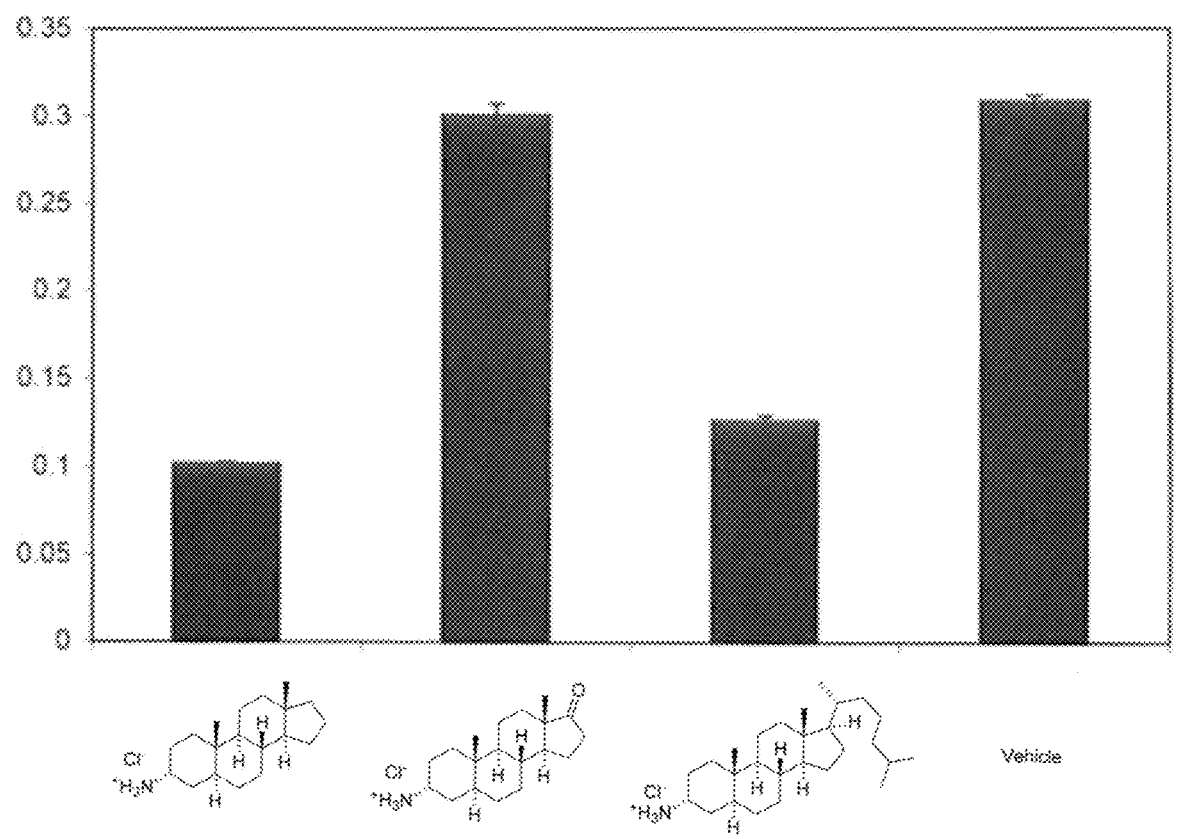
FIG. 3 shows the results of a SHIP malachite phosphatase assay using a UV-Vis plate reader. Absorbance is recorded at 620 nm, smaller numbers indicate a lack of green color and inhibition of the phosphatase.
Figure 4:
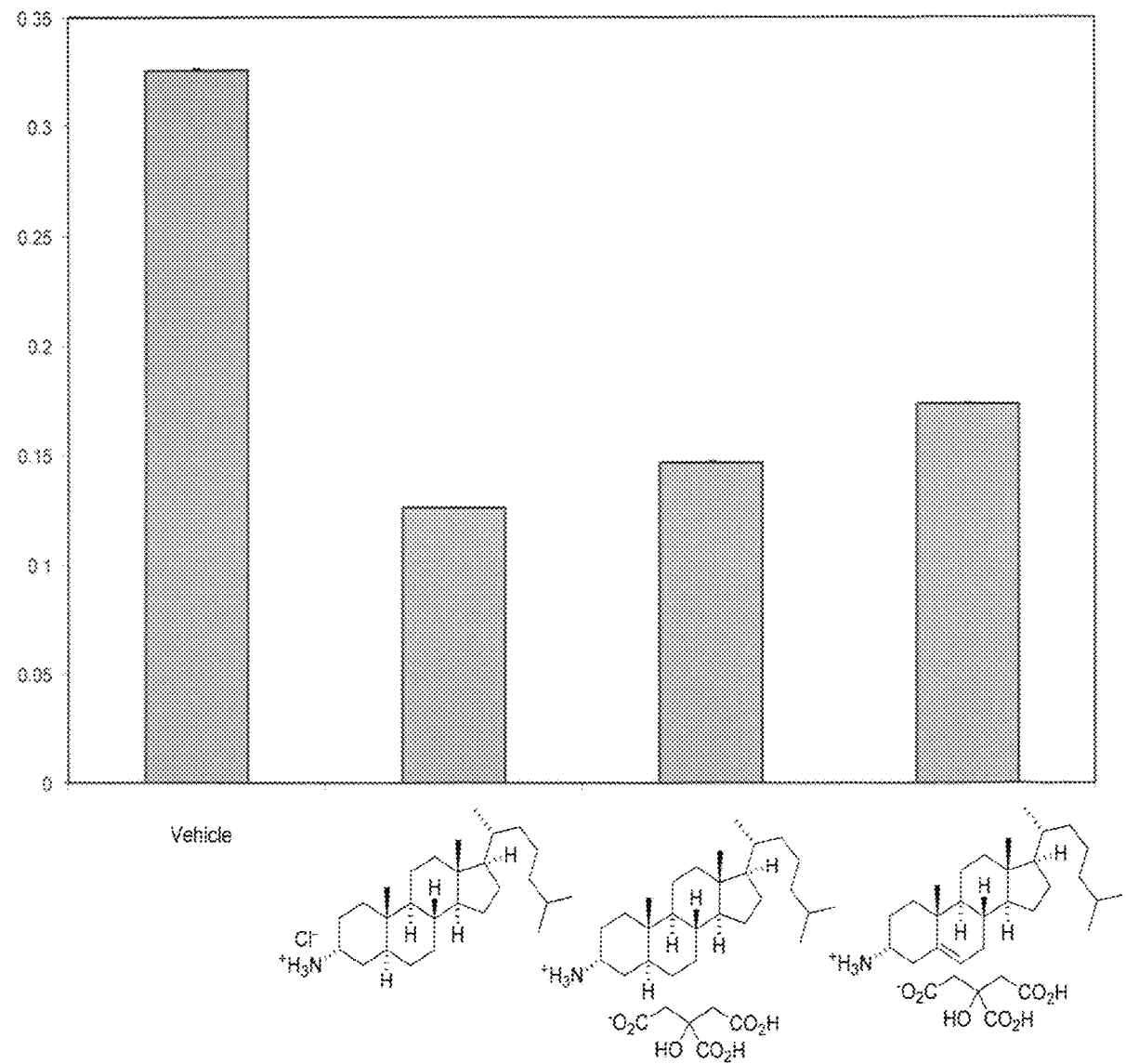
FIG. 4 shows the results of a SHIP malachite phosphatase assay using a UV-Vis plate reader. Absorbance is recorded at 620 nm, smaller numbers indicate a lack of green color and inhibition of the phosphatase.
Figure 5A:
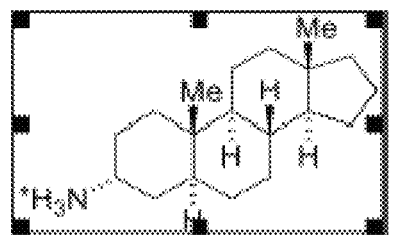
FIG. 5A, FIG. 5B, and FIG. 5C illustrate results of potency studies regarding 3α-amino-5α-androstane (3A5AS). The 3AC derivative, 3A5AS (FIG. 5A), is equally potent for inhibition of recombinant SHIP1 activity in vitro as measured by a Malachite Green assay (see FIG. 5B). However, 3A5AS is more potent for killing of blood cancer cells (C1498 leukemia cells) than the parent compound 3AC as measured in the MTT assay for cell viability (see FIG. 5C).
Figure 5B:
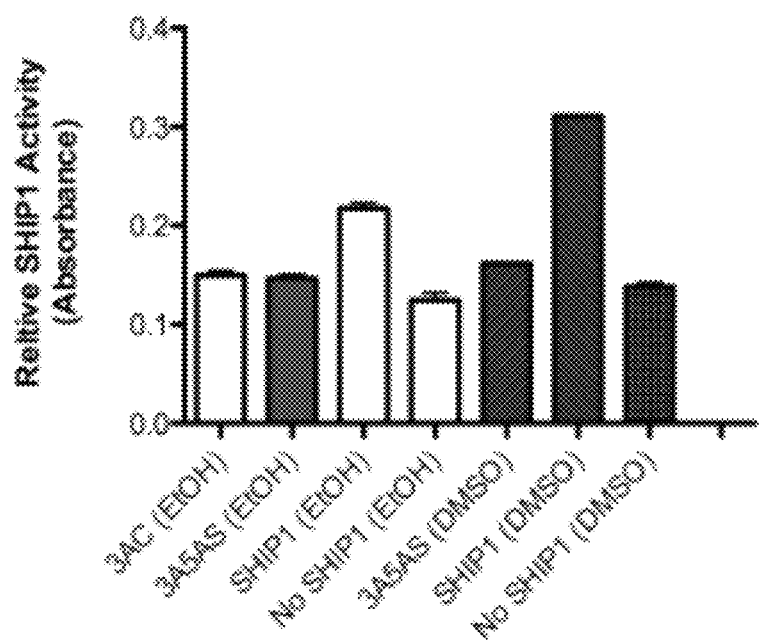
Figure 5C:
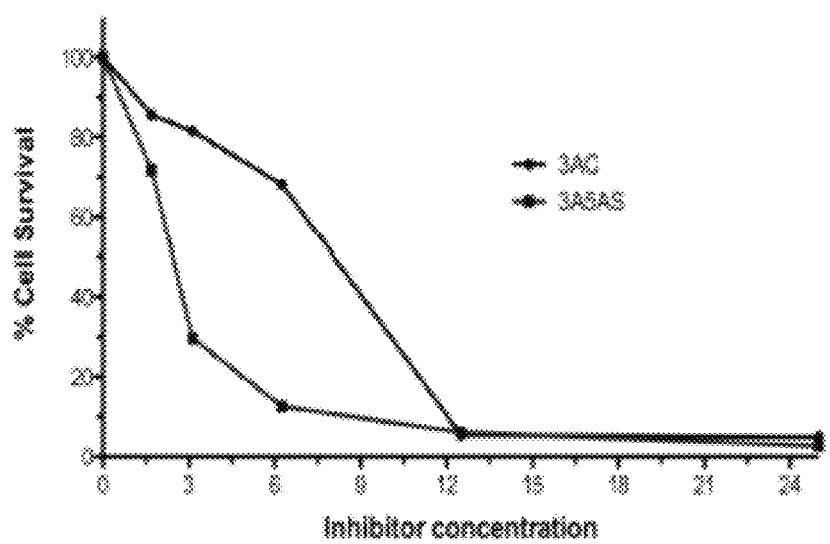

The present invention relates to SHIP inhibitor compounds of the formula (I), and pharmaceutically acceptable salts thereof, where formula (I) is as follows:

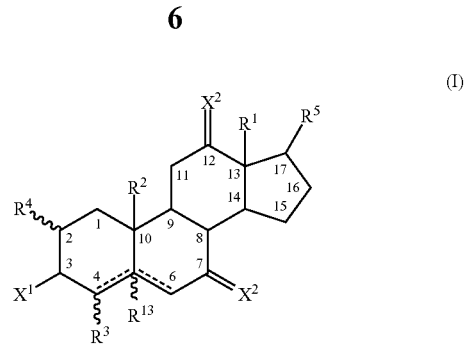

wherein the groups $R^1$, $R^2$, $R^3$, $R^4$, $R^5$, $R^{13}$, $X^1$, and $X^2$ are as hereinafter defined.

The "SHIP inhibitor compounds" of the present invention are also referred to herein as "SHIP inhibitors," "SHIP1 inhibitors," "SHIP1 inhibitor compounds," and the like. In one embodiment, the SHIP inhibitor compounds of the present invention are selective inhibitors of SHIP1.

$R^1$ is a straight chain $C_1$-$C_4$ alkyl or $C_1$-$C_4$ haloalkyl. In one embodiment, $R^1$ is methyl.

$R^2$ is hydrogen, methyl, or halomethyl. In one embodiment, $R^2$ is methyl.

$R^3$ is hydrogen, substituted or unsubstituted amino, $C_1$-$C_4$ alkyl, $C_1$-$C_4$ haloalkyl, or $C_1$-$C_4$ alkenyl. In one embodiment, both $R^3$ and $R^{13}$ are hydrogen.

$R^4$ is hydrogen, hydroxy, substituted or unsubstituted amino, alkyl, or benzyl. In one embodiment, $R^4$ is hydrogen.

$R^5$ includes a divalent oxo atom, or two hydrogen atoms, or one hydrogen atom together with an alkyl group. In one embodiment, $R^5$ represents one hydrogen atom together with an alkyl group. In one embodiment, alkyl group is 1, 5-dimethylhexyl.

$X^1$ may be selected from the group consisting of hydrogen, hydroxy, mercapto, alkoxy, aryloxy, alkylthio, and arylthio. The alkoxy, aryloxy, alkylthio, and arylthio moieties may be further substituted.

$X^1$ may also be selected from the group consisting of alkylcarbonamido, arylcarbonamido, aminocarbonamido, hydrazinocarbonamido, alkylsulfonamido, arylsulfonamido, aminosulfonamido, and hydrazinosulfonamido, all of which may be further substituted.

$X^1$ may also be selected from the group consisting of ($C_1$-$C_4$ alkyl)carbonyloxy, ($C_1$-$C_4$ alkoxy)carbonyloxy, arylcarbonyloxy, aryloxycarbonyloxy, and aminocarbonyloxy, all of which may be further substituted.

$X^1$ may further be selected from the group consisting of a substituted or unsubstituted amino and secondary and tertiary amino groups that include at least one $C_1$-$C_4$ alkyl, $C_5$-$C_6$ cycloalkyl, aryl, or heterocyclic substituent, or combinations thereof. In one embodiment, the secondary or tertiary amino group contains at least one $C_1$-$C_4$ alkyl moiety, which may be further substituted.

$X^1$ may further be an aminoalkyl group, amino($CH_2$)$_n$, where "amino" is an unsubstituted or a substituted secondary or tertiary amino as defined above, and n is an integer from 1 to 4.

$X^1$ may further represent a divalent oxygen moiety, =O, or a divalent N-hydroxyamino moiety, =NOH.

$X^1$ may further be an amino group, except when: $R^1$ and $R^2$ are each methyl; $X^2$, $R^3$, $R^4$, and $R^{13}$ are each hydrogen; and $R^5$ represents one hydrogen atom together with an alkyl group, where the alkyl group is 1, 5-dimethylhexyl alkyl group.

Each $X^2$ is independently defined to represent a divalent oxo or two hydrogen atoms. In one embodiment, each $X^2$ represents two hydrogen atoms.

The compounds of the present invention, as will be appreciated by one skilled in the art, possess several potential chiral carbon atoms. As a consequence of these chiral centers, the compounds of the present invention may occur as racemates, racemic mixtures, individual diastereomers and substantially pure isomers. All asymmetric forms, individual isomers, and combinations thereof, are within the scope of the present invention.

Throughout this specification, the terms and substituents retain their definitions. Below are particular definitions of terms used herein.

The term "alkyl" by itself or as part of another substituent means, unless otherwise stated, a straight or branched chain hydrocarbon radical having the stated number of carbon atoms and includes straight or branch chain groups such as methyl, ethyl, n-propyl, isopropyl, n-butyl, t-butyl, isobutyl, sec-butyl, and higher homologs and isomers such as n-pentyl, n-hexyl, 2-methylpentyl, 1,5-dimethylhexyl, 1-methyl-4-isopropyl, hexyl and the like. A divalent radical derived from an alkane is exemplified by —$CH_2CH_2CH_2CH_2$—. A divalent radical derived from an alkene is exemplified by —CH=CH—$CH_2$—.

The term "alkenyl", employed alone or in combination with other terms, means a straight chain or branched monounsaturated hydrocarbon group having the stated number of carbon atoms, such as, for example, vinyl, propenyl (allyl), crotyl, isopentenyl, and the various butenyl isomers.

Alkyl and alkenyl groups may include substitutents selected from the group consisting of halo, hydroxy, cyano, mercapto, —S($C_1$-$C_4$ alkyl), amino, substituted amino, acetamido, carboxy, trifluoromethyl, $C_1$-$C_4$ alkoxy, ($C_1$-$C_4$ alkoxy)carbonyl and aminocarbonyl.

The term "cycloalkyl" means an unsubstituted or substituted monovalent saturated cyclic hydrocarbon radical having the stated number of carbon atoms, including, various isomers of cyclopentyl and cyclohexyl. The term "cycloalkenyl" means an unsubstituted or substituted monovalent monounsaturated cyclic hydrocarbon radical having the stated number of carbon atoms, including, various isomers of cyclopentenyl and cyclohexenyl. The term "cycloalkadienyl" means a monovalent diunsaturated cyclic radical having the stated number of carbon atoms, including, the various isomers of cyclopentadienyl and cyclohexadienyl. The substituents can be one or two of the same or different substituents selected from halo, hydroxy, cyano, mercapto, —S($C_1$-$C_4$ alkyl), amino, substituted amino, acetamido, carboxy, trifluoromethyl, $C_1$-$C_4$ alkoxy, ($C_1$-$C_4$ alkoxy)carbonyl and aminocarbonyl.

The dotted lines between the 4,5 and 5,6 positions represent the presence or absence of an additional bond; that is, an unsaturation. Only one unsaturation can be present at any one time. The 5 position hydrogen atom and $R^{13}$ shown in Formula (I) will, of course, be absent when an unsaturation is present.

The term "aryl" means an unsubstituted or substituted monovalent phenyl group. The substituents may be independently selected from halo, —OH, —SH, —S($C_1$-$C_4$) alkyl), $C_1$-$C_5$ alkyl, $C_1$-$C_5$ alkoxy, carboxy, ($C_1$-$C_4$ alkoxy)carbonyl, aminocarbonyl, $C_1$-$C_4$ alkylaminocarbonyl, amino, acetamido, $C_1$-$C_4$ alkylamino, di($C_1$-$C_4$ alkyl)amino or a group —$(CH_2)_q$—R where q is 1, 2, 3, or 4 and R is hydroxy, $C_1$-$C_4$ alkoxy, carboxy, $C_1$-$C_4$ alkoxycarbonyl, amino, aminocarbonyl, $C_1$-$C_4$ alkylamino or di($C_1$-$C_4$ alkyl)amino.

The term "benzyl" means a monovalent group in which a phenyl moiety is substituted by a methylene group. The benzyl group may include further substituents on the phenyl moiety.

The term "amino" means a group —$NH_2$. The term, "substituted amino" means an amino group where one or both amino hydrogens are independently replaced by a $C_1$-$C_4$ alkyl, $C_2$-$C_4$ alkenyl, $C_5$-$C_6$ cycloalkyl, $C_5$-$C_6$ cycloalkenyl, aryl, benzyl, or a group —$(CH_2)_q$—R where q is 1, 2, 3, or 4 and R is hydroxy, $C_1$-$C_4$ alkoxy, carboxy, $C_1$-$C_4$ alkoxycarbonyl, amino, aminocarbonyl, $C_1$-$C_4$ alkylamino or di($C_1$-$C_4$ alkyl)amino.

The term "alkylcarbonamido" means a group ($C_1$-$C_4$alkyl)C(O)N(R)—, where R represents H or $C_1$-$C_4$ alkyl. More specifically, the term "acetamido" means a group $CH_3$C(O)NH—. The term "arylcarbonamido" means a group (aryl)C(O)N(R)—, where R represents H or $C_1$-$C_4$ alkyl. The term "aminocarbonamido" means a group R'R"NC(O)N(R)—, where R represents H or $C_1$-$C_4$ alkyl, and R' and R" independently represent H, $C_1$-$C_4$ alkyl, $C_5$-$C_6$ cycloalkyl, aryl, or heterocyclic.

The term "alkylsulfonamido" means a group ($C_1$-$C_4$ alkyl)$SO_2$N(R)—, where R represents H or $C_1$-$C_4$ alkyl. The term "arylsulfonamido" means a group (aryl)$SO_2$N(R)—, where R represents H or $C_1$-$C_4$ alkyl. The term "aminosulfonamido" means a group R'R"NH$SO_2$N(R)—, where R represents H or $C_1$-$C_4$ alkyl, and R' and R" independently represent H, $C_1$-$C_4$ alkyl, $C_5$-$C_6$ cycloalkyl, aryl, or heterocyclic.

The term "alkylcarbonyloxy" means a group ($C_1$-$C_4$ alkyl)C(O)O—. The term "alkoxycarbonyloxy" means a group ($C_1$-$C_4$ alkyl)OC(O)O—. The term "arylcarbonyloxy" means a group (aryl)C(O)O—. The term "aryloxycarbonyloxy" means a group (aryl)OC(O)O—. The term "aminocarbonyloxy" means a group R'R"NC(O)O—, where R' and R" independently represent H, $C_1$-$C_4$ alkyl, $C_5$-$C_6$ cycloalkyl, aryl, or heterocyclic.

The term "halo" means chloro, bromo, fluoro or iodo. The term "mercapto" means a group —SH.

The term "heterocycle" means an unsubstituted or substituted stable 5- or 6-membered monocyclic heterocyclic ring that consists of carbon atoms and from one to three heteroatoms selected from the group consisting of N, O and S, and wherein the nitrogen and sulfur heteroatoms may optionally be oxidized, and the nitrogen heteroatom may optionally be quaternized. The heterocyclic ring may be attached, unless otherwise stated, at any heteroatom or carbon atom that affords a stable structure. The heterocycle may be unsubstituted or substituted with one or two substituents.

In one embodiment of the present invention, the compound of formula (I) is a compound of a formula as set forth below:

Formula 10

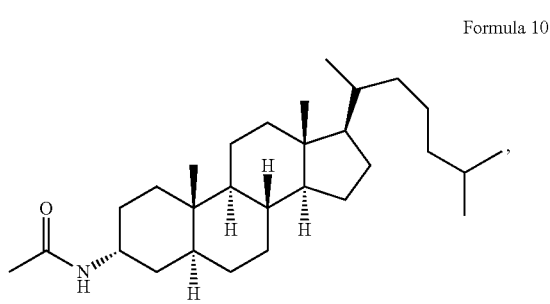

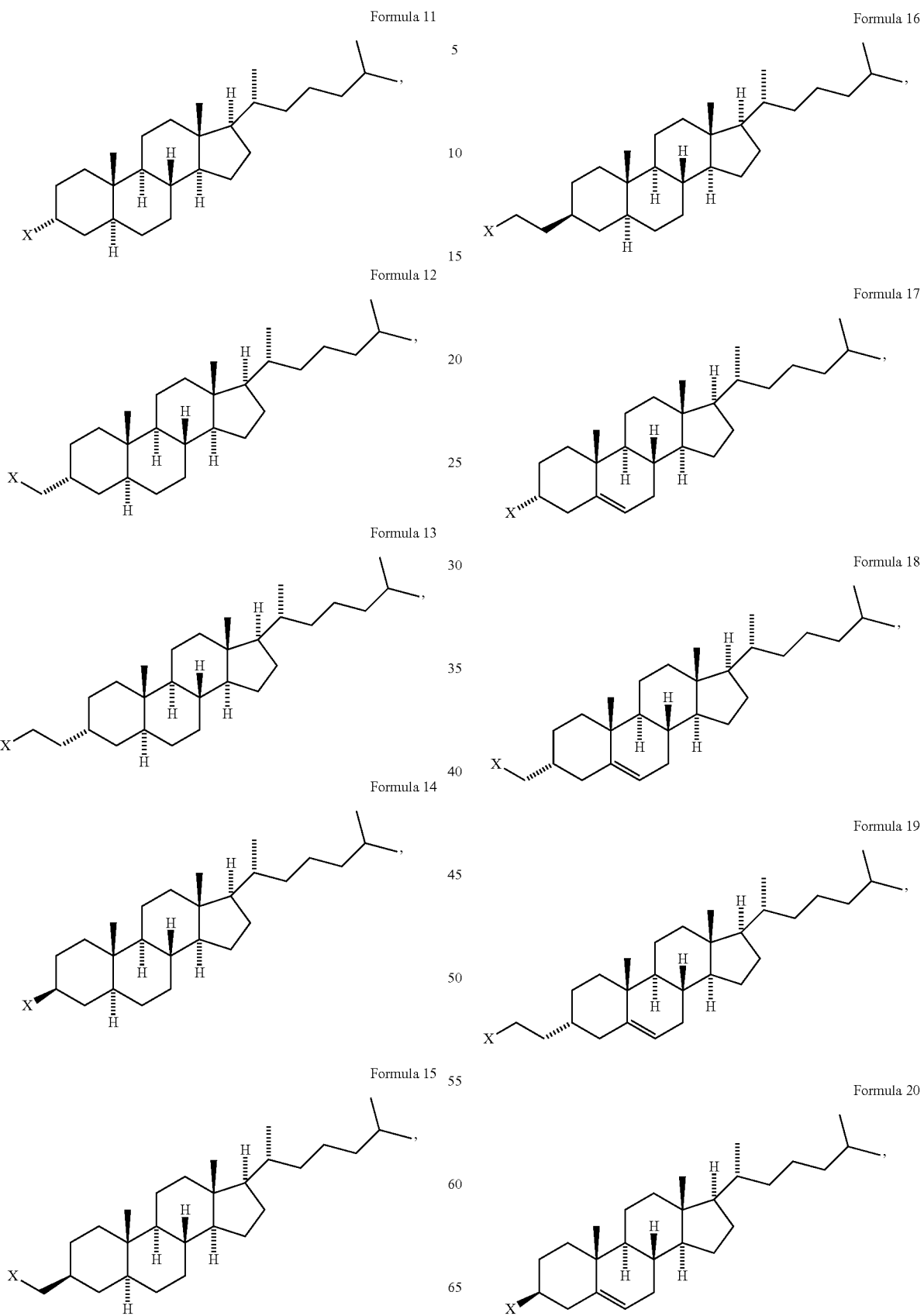

-continued
Formula 21
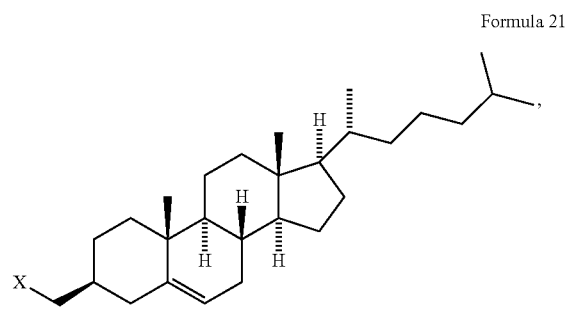
Formula 22
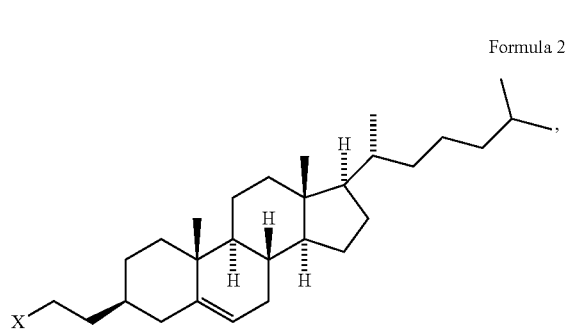
Formula 23
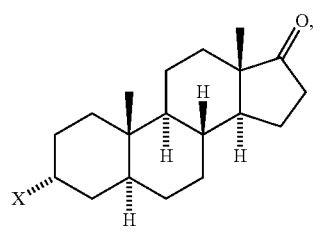
Formula 24
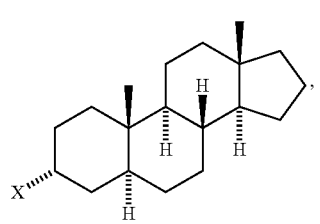
Formula 25
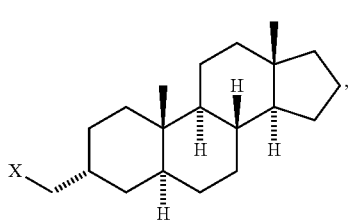
Formula 26
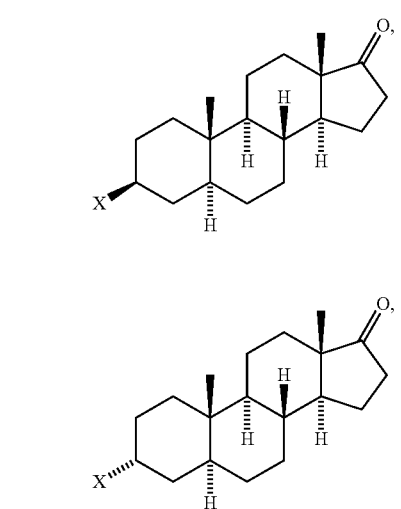
Formula 27
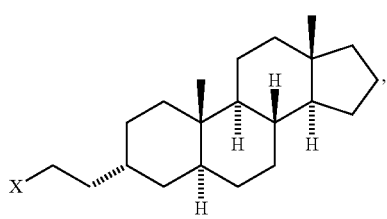
Formula 28
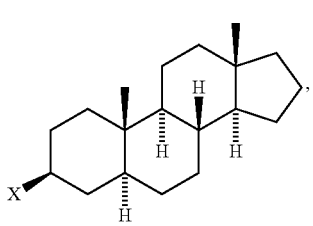
Formula 29
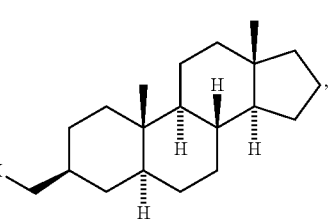
Formula 30
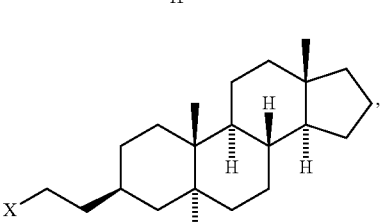
Formula 31
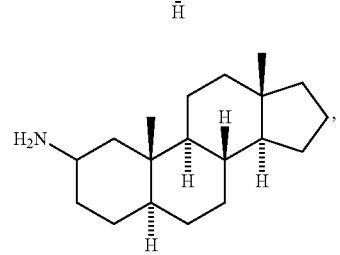
Formula 32
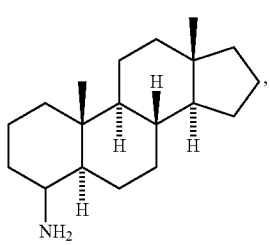
Formula 33
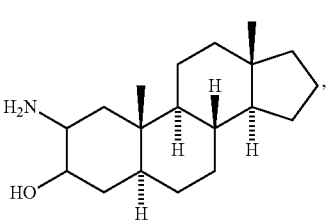

-continued

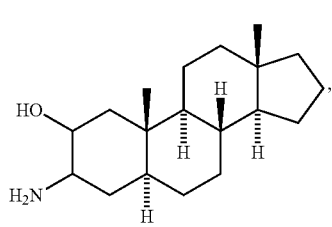

Formula 34

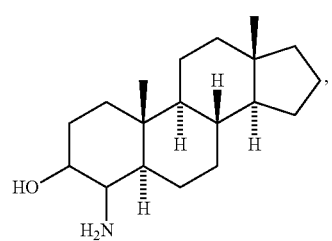

Formula 35

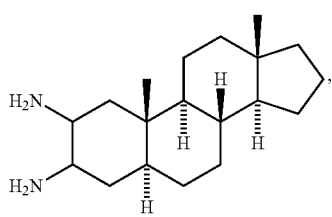

Formula 36

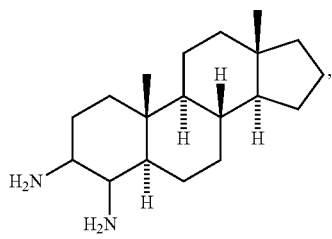

Formula 37 and pharmaceutically acceptable salts thereof, wherein X=NR2, NRCOR, NHCONR2, OR, SR, OCOR, OCONR2, or NHCNHNH2, and wherein R=H, alkyl, cycloalkyl, aryl, or benzyl.

The present invention provides methods for prevention and clinical treatment of various forms of graft-versus-host disease (GVHD) by using inhibitors of SH2-domain containing inositol phosphatase (SHIP). In particular, novel formulations of SHIP inhibitors are provided for the treatment in order to suppress T-lymphocyte mediated immune responses.

SHIP1-deficiency has been linked to transplant tolerance in genetic studies. Accordingly, molecular targeting of SHIP1 can be utilized to achieve similar effects, including an increase in immunoregulatory capacity. The SHIP1 inhibitor compounds of the present invention provide such molecular targeting. Treatment with the SHIP1 inhibitor compounds of the present invention significantly expands the myeloid immunoregulatory cell compartment and impairs the ability of peripheral lymphoid tissues to prime allogeneic T cell responses. In addition, treatment with the SHIP1 inhibitor compounds of the present invention profoundly increases granulocyte production without triggering the myeloid-associated lung consolidation observed in SHIP1$^{+/-}$ mice. It was also found that chemical inhibition of SHIP1 triggers apoptosis of blood cancer cells. Thus, SHIP1 inhibitors of the present invention provide a novel class of small molecules that have the potential to enhance allogeneic transplantation, boost innate immunity, and improve the treatment of hematologic malignancies.

SHIP is critical in cell-mediated allogeneic immune responses, and SHIP deficient hosts do not support priming of allogeneic T cell responses. Targeting SHIP facilitates allogeneic transplantation. It is also believed that the SHIP1 inhibitor compounds of the present invention can also inhibit SHIP2, a potential molecular target in diabetes, but not PTEN. It is further believed that the SHIP1 inhibitor compounds of the present invention can also inhibit the ability of peripheral lymphoid tissues to prime allogeneic T cell responses in vitro. It is believed that administration of the SHIP1 inhibitor compounds of the present invention expands the number of both myeloid and T lymphoid immunoregulatory cells in secondary lymphoid tissues where GvHD is primed and expands the number of NK cells in the periphery of models. Such results demonstrate the enzymatic activity of SHIP is required for the priming of allogeneic T cells responses.

The SHIP1 inhibitor compounds of the present invention described and identified herein are believed to significantly inhibit the enzymatic activity of SHIP in solution. To further validate that compounds identified in the solution based assay for SHIP activity are cell permeable and can alter the immune system in a manner comparable to that observed in SHIP deficient mice, the ability of some of the more potent SHIP inhibitors can be tested to inhibit priming of an allogeneic T cell response in vitro and for the ability to expand immunoregulatory cell populations and to abrogate GvHD. A potent inhibitor of SHIP in solution is also shown to inhibit priming of an allogeneic T cell response as measured in an MHC-mismatched MLR and can significantly expand the number of myeloid and T lymphoid immunoregulatory cells in secondary lymphoid tissues.

That SHIP inhibitors identified via a HTS screen can impair priming of allogenic T cells responses in vitro and can expand immunoregulatory cells in lymphoid tissues suggests that chemical inhibition of SHIP activity could be utilized to facilitate allogeneic transplantation procedures. Therefore, the SHIP1 inhibitor compounds of the present invention are useful to enhance engraftment of allogeneic BM as Treg cells are known to not only combat GvHD, but can also facilitate engraftment of donor BM in MHC-mismatched transplant settings. In addition, expansion of myeloid derived suppressor cell (MDSC) and Treg cell numbers also reduces the frequency that donor T cells are primed by host antigen presenting cells (APC) in secondary lymphoid tissues and, thus reduces the incidence and severity of GvHD. As solid organ graft responses by host T cells are also primed in secondary lymphoid tissues, and Treg cells also facilitate solid organ graft acceptance, the SHIP inhibitors of the present invention will prove useful for reducing organ graft rejection. As SHIP-deficient mice exhibit normal humoral immunity and APC priming of T cell response to foreign antigens, the compounds described herein spare normal adaptive immune function. Thus, they offer a more selective method to dampen deleterious host and donor allogenic T cell responses without compromising adaptive immune functions necessary to combat opportunistic pathogens that frequently infect transplant patients undergoing conventional immunosuppressive therapies.

SHIP inhibition also prevents chemo-attraction of tumor cells to directed tissues in vivo. SDF1 serves as a chemo-attractant to lure stem cells and tumor cells into tissue sites, referred to as metastasis for tumor cells. There is very little or no SDF1/CXCL 12 produced in BM (bone marrow) or solid organs (e.g. spleen) in SHIP-deficient mice. Thus, SHIP inhibitors may be administered to shut down or significantly reduce production of SDF1/CXCL12 in tissues and organs. The SHIP inhibitors are also useful to inhibit tumor growth and metastasis in solid organs and tissues.

The present disclosure further describes the identification and initial in vivo characterization of small molecule inhibitors of the SHIP1 enzyme. To validate that these compounds are cell permeable and can alter the immune system in a manner comparable to that observed in SHIP1 deficient mice, their ability to expand MIR cells and to consequently inhibit priming of an allogeneic T cell response was tested. It is shown herein that chemical inhibition of SHIP1 is capable of both. In addition, SHIP1 inhibition promotes a profound increase in circulating granulocyte numbers and apoptosis of blood cancer cells.

It is also shown that administration of a SHIP1 inhibitor can expand immunoregulatory cells in peripheral lymphoid tissues and suppress priming of allogeneic T cell responses. Because allogeneic T cell responses that culminate in GvHD or solid organ graft rejection are primed in peripheral lymphoid tissues, [Lafferty K J, et al., Surg Clin North Am (1986) 66(6):1231-1253; Kosaka H, et al., J Exp Med (1992) 176(5):1291-1302; Shlomchik W D, et al., Science (1999) 285(5426):412-415] these results show that the SHIP inhibitor compounds of the present invention can potentially be used to limit deleterious T cell responses that mediate GvHD and organ graft rejection. Consistent with this, GvHD is reduced and cardiac graft rejection delayed in adult mice rendered SHIP1-deficient [Paraiso K H, et al., J Immunol (2007) 178(5):2893-2900; Collazo M M, et al., Blood (2009) 113:2934-2944]. As SHIP1-deficient mice exhibit normal humoral immunity [Brauweiler A, et al., J Exp Mad (2000) 191(9):1545-1554; Liu Q, et al., J Exp Med (1998) 188(7):1333-1342] and priming of T cell responses to naive antigens [Ghansah T, et al., J Immunol (2004) 173(12):7324-7330], the SHIP1 inhibitor described here, and potentially others, may not significantly compromise adaptive immune function. Thus, the SHIP1 inhibitor compounds of the present invention offers a more selective method to dampen deleterious host and donor allogeneic T cell responses without compromising adaptive immune functions necessary to combat opportunistic pathogens that can compromise the recovery and survival of transplant patients receiving state-of-the-art immunosuppressive regimens.

Increased Akt signaling and survival in primary NK [Wang J W, et al., Science (2002) 295(5562):2094-2097] and myeloid cells [Liu A, et al., Genes & Development (1999) 13(7):786-791] isolated from SHIP1$^{+/-}$ mice have been documented. However, there is also an emerging role for the SHIP1/2 product PI(3,4)P$_2$ in promoting Akt activation [Franke T F, et al., Science (1997) 275(5300):665-668] and tumorigenicity. [Ivetac I., et al., EMBO Rep (2009) 10(5):487-493] Thus, via generation of PI(3,4)P$_2$, SHIP1/2 could amplify survival signals in transformed or neoplastic cells by providing additional plasma membrane locations for recruitment and activation of PH-domain containing kinases, such as Akt. Indeed, PI(3,4)P$_2$ levels are found to be increased in leukemia cells. [Jain S K, et al., Blood (1996) 88(5):1542-1550] Consistent with this hypothesis, it is shown that a SHIP1 selective inhibitor reduces Akt activation and promotes apoptosis of human blood cell cancers that express SHIP1. Thus, SHIP1 inhibition can be used as an adjunct to other therapeutics to further decrease the survival of hematologic malignancies. There will also be applications for SHIP1/2 inhibitors in non-hematologic cancers as SHIP2 expression is increased in breast cancer and promotes survival signals from EGF-R in these cells. [Prasad N K, et al., Tumour Bioi (2008) 29(5):330341; Prasad N K, et al., Carcinogenesis (2008) 29(1):25-34; Prasad N K, Int J Onool (2009) 34(1):97-105]

Although treatment of mice with a SHIP selective inhibitor induced many of the same myeloid phenotypes observed in mice that are genetically SHIP1-deficient, some key deleterious effects associated with genetic SHIP1 deficiencies were notably absent. Importantly, we did not to observe myeloid lung consolidation and pneumonia emerging in inhibitor-treated mice. This could be fortuitous, since this pneumonia is the major pathology that limits the lifespan of SHIP1$^{+/-}$ mice. [Helgason C D, et al. (1998) Genes & Development 12(11):1610-1620] Without wishing to be bound to a particular theory, there are several reasons that chemical inhibition of SHIP1 enzymatic activity and germline SHIP1 deficiency do not result in identical hematologic manifestations. In germline SHIP1-deficient mice there is complete loss of SHIP1 protein from the point of conception and, thus, the developmental effects of SHIP1-deficiency may trigger some abnormalities that may not occur in the treatment of adult mice with a SHIP inhibitor. Although it has been documented that several SHIP1 phenotypes are induced in MxCreSHIP1$^{flox/flox}$ mice rendered SHIP1-deficient as adults, [Ghansah T, et al., J Immunol (2004) 173(12):7324-7330; Hazen A L, et al., Blood (2009) 113(13):2924-2933; Collazo M M, et al., Blood (2009) 113:2934-2944] these mice have not been examined for lung pathology. Another possible explanation for the difference between chemical and genetic ablation of SHIP1 function is that a SHIP1 null mutation results in the absence of SHIP1 protein. The absence of SHIP1 protein has the potential to permit inappropriate activities by other signaling proteins that assume its place in cell signaling complexes. In fact, this is known to occur in SHIP1$^{+/-}$ NK cells, as loss of SHIP1 expression leads to inappropriate recruitment of SHP1 to the 2B4 SLAM family receptor converting this receptor from activating mode to a dominant inhibitory mode. [Wahle J A, et al., J Immunol (2007) 179(12):8009-8015] It is possible then that the myeloid lung consolidation observed in SHIP1$^{+/-}$ mice also results from inappropriate activity by another signaling protein that fills the void left by the absence of SHIP1 protein. Further analysis of these questions could provide mechanistic insights into the role that SHIP1 plays in alveolar macrophage biology.

In addition to the above effects relevant to allogeneic transplantation, SHIP1 inhibitors will also offer benefits to cancer patients. For instance, a SHIP1 inhibitor could be used to enhance granulocyte recovery after autologous BMT or high dose chemo/radiotherapy that frequently compromises granulocyte production and function. Granulocytes serve as the first line of defense against bacterial, fungal and parasitic infections and thus play a prominent role in recovery following myeloablative therapies. In addition, the growth and survival of SHIP1-expressing blood cell malignancies is significantly reduced by chemical inhibition of SHIP1. Thus, the SHIP inhibitor compounds of the present invention represent a novel class of compounds that could potentially find utility in both transplantation and the treatment of cancer.

In one embodiment, a method is provided for treating a patient suffering from GVHD. The method comprises administering to the GVHD patient a composition including a SHIP1 inhibitor compound of the present invention.

Dosage amounts and frequency will vary according to the particular SHIP inhibitor, the dosage form, and individual patient characteristics. Generally speaking, determining the dosage amount and frequency for a particular SHIP inhibitor, dosage form, and individual patient characteristic can be accomplished using conventional dosing studies, coupled with appropriate diagnostics.

In a particular embodiment, a SHIP inhibitor is used to treat patients that have acute Graft vs Host Disease (aGVHD) but failed at least one immunosuppressive regimen such as a regimen including steroids such as prednisone and methylprednisolone, cyclophosphamide, cyclosporin A, FK506, thalidomide, azathioprine, and daclizumab. For example, hematopoietic stem cell transplant (HSCT) patients manifesting grade 2 or greater aGVHD, who have failed to respond to treatment with at least 2 mg/Kg of methylprednisolone or equivalent corticosteroid or other salvage therapy, can be treated with a SHIP1 inhibitor.

A SHIP inhibitor of the present invention can also be used as a prophylaxis to prevent onset of GVHD or to reduce the effects of GVHD.

A SHIP inhibitor of the present invention may be administered as a GVHD prophylaxis to a transplant recipient within a predetermined time window before or after the transplantation.

In one embodiment, a SHIP inhibitor of the present invention may be administered to the recipient on days −3 or −2 (i.e., 3 or 2 days before the transplantation) as part of a non-myeloablative conditioning regimen, then followed by transplantation such as hematopoietic stem cell infusion. Alternatively, a SHIP inhibitor of the present invention may be administered as a GVHD prophylaxis to a transplant recipient after the transplantation. For example, for standard (i.e., myeloablative) transplant or non-myeloablative stem cell transplant (NST) where a SHIP inhibitor of the present invention is not used in the conditioning regimen, a SHIP inhibitor of the present invention is administered to the transplant recipient at 0.5-1.5 mg/m$^2$/day on days +8, +15, +22, and +30 following stem cell infusion.

Besides use in a single-agent treatment or prevention of GVHD, a SHIP inhibitor of the present invention can also be used in a combination therapy for acute or chronic GVHD. The combination therapy may have synergistic therapeutic effects on the patients and thus requires lower amount of the SHIP inhibitor of the present invention and the other agent used in conjunction to achieve satisfactory therapeutic efficacy. As a result, potential side effects associated with high dose of drugs, such as myelosuppression, are reduced and the patient's quality of life is improved.

Various other therapeutic agents may be combined with the SHIP inhibitor for the treatment or prevention of GVHD. The other therapeutic agents include, but are not limited to, immunosuppressive agents such as steroids (e.g., prednisone and methylprednisolone), cyclophosphamide, cyclosporin A, FK506, thalidomide, azathioprine, monoclonal antibodies (e.g., Daclizumab (anti-interleukin (IL)-2), Infliximab (anti-tumor necrosis factor), MEDI-205 (anti-CD2), abx-cbl (anti-CD147), and polyclonal antibodies (e.g., ATG (anti-thymocyte globulin)). For example, a SHIP inhibitor of the present invention may be combined with a steroid such as methylprednisolone to treat GVHD. However, such a combination may be too broadly immunosuppressive to render the patient more susceptible to opportunistic infection.

For the treatment of acute GVHD, a SHIP inhibitor of the present invention may preferably be combined with monoclonal antibodies which specifically target T-cells such as Infliximab, Daclizumab, MEDI-205, or abx-cbl. The monoclonal antibody may be administered at the FDA-approved dosage and by its standard route of administration (e.g., IV), followed by oral or parenteral administration of a SHIP inhibitor of the present invention.

The SHIP inhibitor may also be used in conjunction with other immunosuppressive agents as prophylaxis for GVHD post-transplantation. For example, the recipient of bone marrow transplant may be treated with a SHIP inhibitor of the present invention in conjunction with a standard post infusion regimen including mini-methotrexate at 5 mg/m$^2$ (as opposed to the conventional dose at 10-15 mg/m$^2$), cyclosporine A (5-6 mg/Kg/d IV or 10-18 mg/Kgld orally) and FK506 (0.05-0.1 mglKg/d IV or 0.15-0.3 mg/Kg/d orally).

In addition, a SHIP inhibitor of the present invention may be used in conjunction with other types of therapy as prophylaxis for GVHD prior to transplantation. For example, the recipient of bone marrow transplant may be pretreated with a SHIP inhibitor of the present invention in conjunction with TBI (radiation), phototherapy, melphalan, cyclophosphamide or ATG to prevent the onset of GVHD.

In yet another aspect, the invention relates to a method of ex vivo or in vitro treatment of blood derived cells, bone marrow transplants, or other organ transplants. The method comprises treating the blood derived cells, bone marrow transplants, or other organ transplants with a SHIP inhibitor of the present invention in an effective amount such that activities of T-lymphocytes therein are substantially inhibited, particularly by at least 50% reduction in activity, more particularly by at least 80% reduction in activity, and further more particularly by at least 90% reduction in activity.

The invention is practiced in an in vitro or ex vivo environment. All of the discussion above regarding clinical treatment or prevention of GVHD that is relevant to an in vitro or ex vivo environment applies to this practice. In a particular embodiment, practice of an in vitro or ex vivo embodiment of the invention might be useful in the practice of immune system transplants, such as bone marrow transplants or peripheral stem cell procurement. In such procedures, the SHIP inhibitor might be used, as generally described above, to treat the transplant material to inactivate T-lymphocytes therein so that the T-lymphocyte mediated immune response is suppressed upon transplantation.

For example, a SHIP inhibitor of the present invention may be added to a preservation solution for an organ transplant in an amount sufficient to inhibit activity of T-lymphocytes of the organ. Such a preservation solution may be suitable for preservation of different kind of organs such as heart, kidney and liver as well as tissue therefrom. An example of commercially available preservation solutions is Plegisol (Abbott), and other preservation solutions named in respect of its origins include the UW-solution (University of Wisconsin), the Stanford solution and the Modified Collins solution. The preservation solution may also contain conventional co-solvents, excipients, stabilizing agents and/or buffering agents.

The dosage form of the SHIP inhibitor of the present invention may be a liquid solution ready for use or intended for dilution with a preservation solution. Alternatively, the dosage form may be lyophilized or power filled prior to reconstitution with a preservation solution. The lyophilized substance may contain, if suitable, conventional excipients.

The preservation solution or buffer containing a SHIP inhibitor of the present invention may also be used to wash or rinse an organ transplant prior to transplantation or storage. For example, a preservation solution containing pentostatin may be used to flush perfuse an isolated heart which is then stored at 4°.

In another embodiment, practice of the invention might be used to condition organ transplants prior to transplantation. Prior to transplantation a SHIP inhibitor of the present invention may be added to the washing buffer to rid the transplant of active T-lymphocytes. In this way, the risk of developing acute GVHD upon transplantation should be significantly reduced, and the host is not only protected from GVHD but also from potential side effects of the SHIP inhibitor. The concentration of the SHIP inhibitor in the preservation solution or wash buffer may vary according to the type of transplant. Other applications in vitro or ex vivo using a SHIP inhibitor of the present invention will occur to one of skill in the art and are therefore contemplated as being within the scope of the invention.

Other than in the operating examples, or unless otherwise expressly specified, all of the numerical ranges, amounts, values and percentages such as those for amounts of materials, times and temperatures of reaction, ratios of amounts, values for molecular weight (whether number average molecular weight ("$M_n$") or weight average molecular weight ("$M_w$"), and others in the following portion of the specification may be read as if prefaced by the word "about" even though the term "about" may not expressly appear with the value, amount or range. Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

As used herein, the term "pretreating" (or "pretreatment") is intended to mean that a first treatment is administered prior to, or in conjunction with, a second treatment. In other words, the pretreatment may be performed before another, later treatment, thus allowing the pretreatment time to take effect. Alternatively, the pretreatment may be performed or administered simultaneously with a second treatment without a temporal delay. Advantageously, a pretreatment is administered prior to a second treatment.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prod rug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

As used herein, "treatment" refers to obtaining beneficial or desired clinical results. Beneficial or desired clinical results include, but are not limited to, anyone or more of: alleviation of one or more symptoms (such as tumor growth or metastasis), diminishment of extent of cancer, stabilized (i.e., not worsening) state of cancer, preventing or delaying spread (e.g., metastasis) of the cancer, preventing or delaying occurrence or recurrence of cancer, delay or slowing of cancer progression, amelioration of the cancer state, and remission (whether partial or total). The methods of the invention contemplate anyone or more of these aspects of treatment.

A "subject in need of treatment" is a mammal with a condition that is life-threatening or that impairs health or shortens the lifespan of the mammal.

A "pharmaceutically acceptable" component is one that is suitable for use with humans and/or animals without undue adverse side effects (such as toxicity, irritation, and allergic response) commensurate with a reasonable benefit/risk ratio.

A "safe and effective amount" refers to the quantity of a component that is sufficient to yield a desired therapeutic response without undue adverse side effects (such as toxicity, irritation, or allergic response) commensurate with a reasonable benefit/risk ratio when used in the manner of this invention.

A "pharmaceutically acceptable carrier" is a carrier, such as a solvent, suspending agent or vehicle, for delivering the compound or compounds in question to the animal or human. The carrier may be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods. See, generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4th Ed, John Wiley & Sons, Inc.; as well as Guthrie et al., Guide to Yeast Genetics and Molecular Biology, Methods in Enzymology, Vol. 194, Academic Press, Inc., (1991), PCR Protocols: A Guide to Methods and Applications (Innis, et al. 1990. Academic Press, San Diego, Calif.), McPherson et al., PCR Volume 1, Oxford University Press, (1991), Culture of Animal Cells: A Manual of Basic Technique, 2nd Ed. (R. I. Freshney. 1987. Liss, Inc. New York, N.Y.), and Gene Transfer and Expression Protocols, pp. 109-128, ed. E. J. Murray, The Humana Press Inc., Clifton, N.J.).

In addition to the applications described above, the SHIP inhibitor compounds of the present invention can be used for various other applications, particularly regarding treatment of conditions that follow chemotherapy, radiation therapy, or infection, or that occur in myelodysplastic/bone failure patients. Such conditions can include, without limitation, myelosuppression, anemia, and the lack of platelets. For example, the SHIP inhibitors of the present invention may be used to boost production of all key blood cell types as well as white blood cells and lymphocytes. The SHIP inhibitors of the present invention may also be used for patients recovering from either an autologous or allogenic bone marrow transplant to enhance recovery of key blood cell components after transplant. Various growth factors known in the art can be combined with the SHIP inhibitors of the present invention in a combination therapy, e.g., to boost neutrophils/granulocytes, red blood cells, and platelets in a subject. Further, the SHIP inhibitors of the present invention may be used to enhance blood stem cell harvest, e.g., SHIP inhibitors have been shown to mobilize a radioprotective dose of such stem cells from the bone marrow to the blood.

In view of the above, below are various other aspects of the present invention.

In another aspect, the present invention relates to a method of treating myelosuppression in a subject. This method includes the step of administering to the subject one or more SHIP1 inhibitor compound of the present invention under conditions effective to treat myelosuppression in the subject.

In another aspect, the present invention relates to a method of treating anemia in a subject. This method includes the step of administering to the subject one or more SHIP1 inhibitor compound of the present invention under conditions effective to treat anemia in the subject.

In another aspect, the present invention relates to a method of increasing platelets in a subject. This method includes the step of administering to the subject one or more SHIP1 inhibitor compound of the present invention under conditions effective to increase platelets in the subject.

In another aspect, the present invention relates to a method of aiding recovery of a subject who has undergone a bone marrow transplant. This method includes the step of administering to the subject one or more SHIP1 inhibitor compound of the present invention under conditions effective to increase production in the subject of blood cell components, thereby aiding the post-bone marrow transplant recovery of the subject. This method can be used to aid the recovery of subjects who have undergone an autologous bone marrow transplant or an allogenic bone marrow transplant. In one embodiment, this method can further include administering at least one growth factor to the subject along with the one or more SHIP1 inhibitor compound.

In another aspect, the present invention relates to a method of enhancing blood stem cell harvest from a subject. This method includes the step of administering to the subject one or more SHIP1 inhibitor compound of the present invention under conditions effective to mobilize stem cells in the subject from the bone marrow to the blood.

EXAMPLES

The following examples are intended to illustrate particular embodiments of the present invention, but are by no means intended to limit the scope of the present invention.

Example 1

Synthesis of 3α-Acetamido-5α-Cholestane

The 3α-acetamido-5α-cholestane of the present invention can be made using the following synthetic scheme:

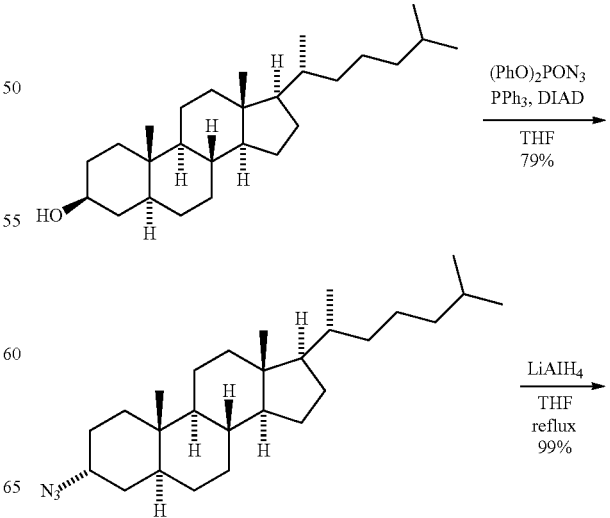

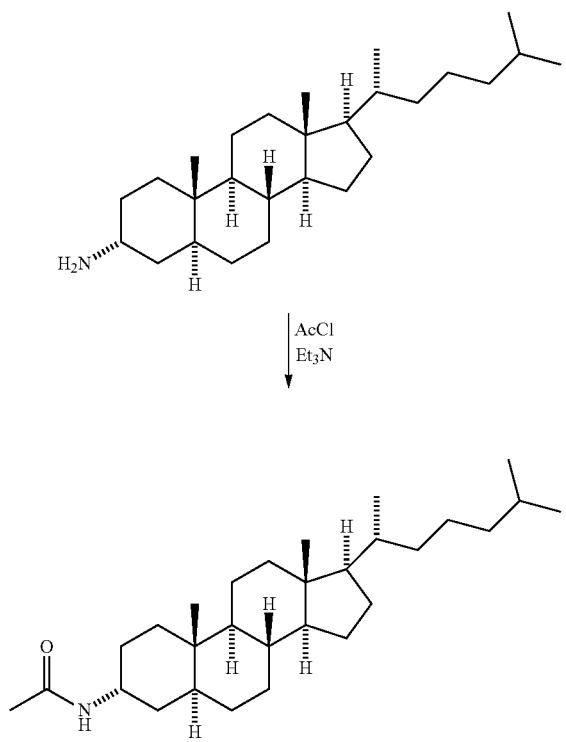

Example 2

Experimental Data Relating to
3α-Acetamido-5α-Cholestane

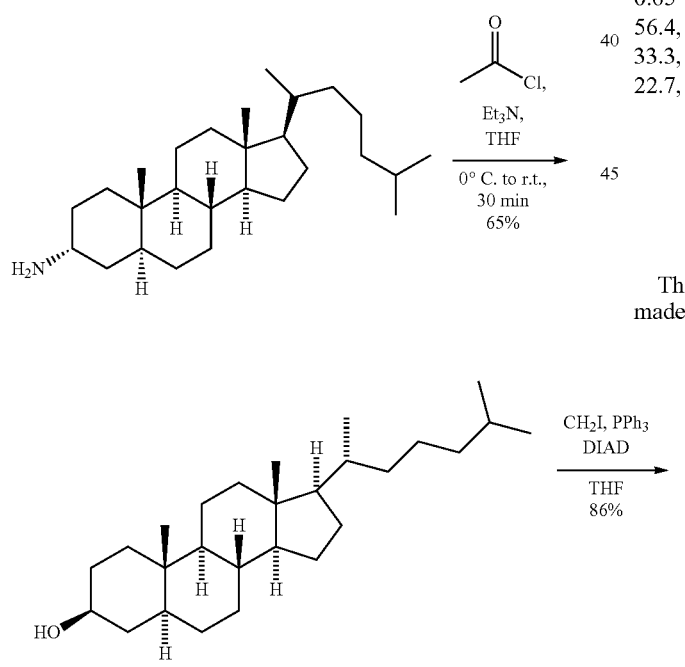

3α-Acetamido-5α-cholestane. The α-amine (0.29 g, 0.75 mmol) was dissolved THF (2.21 mL) in a round bottom flask. Et$_3$N (0.12 mL, 0.90 mmol) was added dropwise and the resulting solution was cooled at 0° C. Acetyl chloride (0.06 mL, 0.83 mmol) was added dropwise into the cooled solution which resulted on the formation of white precipitate. The milky white solution was stirred continuously for 15 min at 0° C. before allowing the reaction mixture to warm up to room temperature. THF (5 mL) was added and the diluted solution was washed with HCl (10 mL, 1 M), brine solution (10 mL), and H$_2$O (10 mL). The organic layer was collected, dried over Na$_2$SO$_4$, and concentrated under reduced pressure. Recrystallization of the solid residue using EtOH afforded amide (0.22 g, 65%) as off white solid.

IR (KBr): 3265, 2931, 2864, 2848, 1667, 1337 cm$^{-1}$. m.p.=215-216° C. $^1$H NMR (300 MHz, CDCl$_3$): δ 5.71 (broad, 1H), 4.13 (broad, 1H), 1.99 (s, 3H), 1.96 (t, J=3 Hz, 1H), 1.79 (m 1H), 1.60-1.65 (m, 2H), 1.45-1.60 (m, 7H), 1.31-1.36 (m, 6H), 1.27-1.28 (m, 1H), 1.03-1.04 (m, 2H), 0.96-1.00 (m, 5H), 0.94-0.96 (m, 1H), 0.87 (s, J=1.2 Hz, 3H), 0.85 (d, J=1.2 Hz, 3H), 0.80 (s, 3H), 0.68-0.73 (m, 1H), 0.65 (s, 3H). $^{13}$C NMR (75 MHz, CDCl$_3$): δ 169.4, 56.7, 56.4, 54.7, 44.9, 42.7, 41.0, 40.2, 39.6, 36.3, 36.1, 35.9, 35.5, 33.3, 33.0, 32.1, 28.6, 28.4, 28.1, 26.1, 24.3, 24.0, 23.8, 23.0, 22.7, 20.9, 18.8, 12.2, 11.6

Example 3

Synthesis of the β-Amine Compound

The β-amine compound of the present invention can be made using the following synthetic scheme:

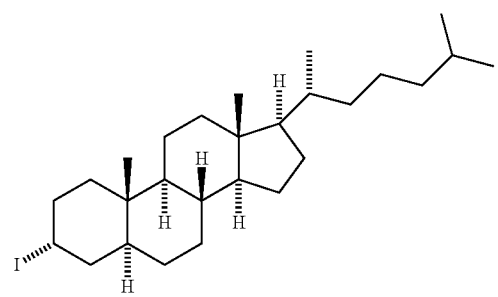

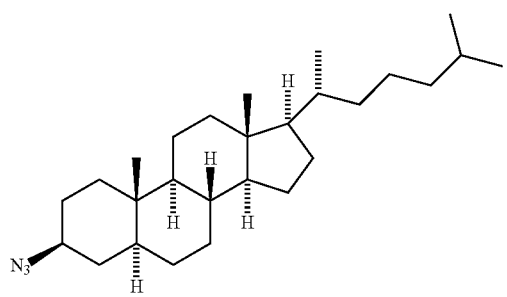

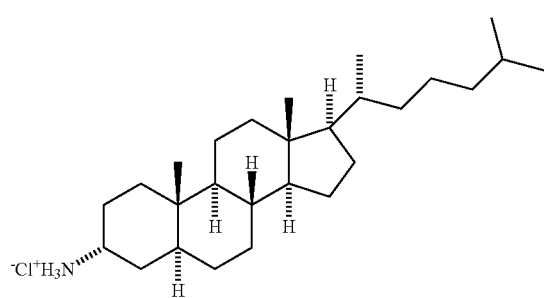

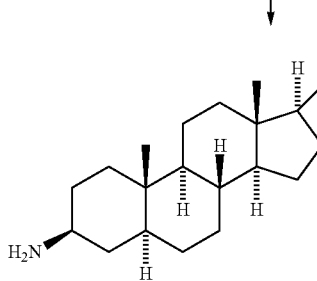

Example 4

Analogs

Various analogs are contemplated as being SHIP inhibitors of the present invention, as described below:

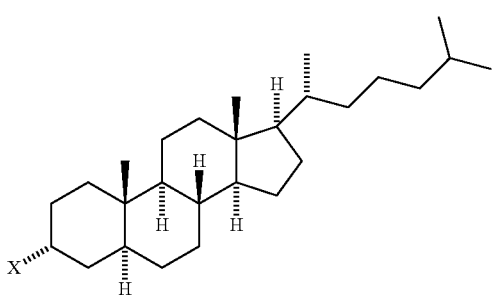

X = $NR_2$, NRCOR, $NHCONR_2$
OR, SR, OCOR, $OCONR_2$, $NHCNHNH_2$
R = H, alkyl, cycloalkyl, aryl, benzyl
also should cover salts of the amine

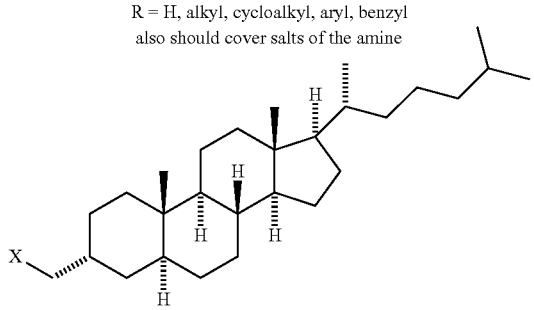

X = $NR_2$, NRCOR, $NHCONR_2$
OR, SR, OCOR, $OCONR_2$, $NHCNHNH_2$
R = H, alkyl, cycloalkyl, aryl, benzyl
also should cover salts of the amine

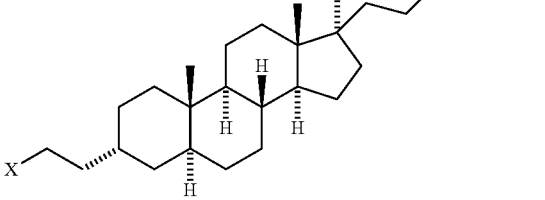

X = $NR_2$, NRCOR, $NHCONR_2$
OR, SR, OCOR, $OCONR_2$, $NHCNHNH_2$
R = H, alkyl, cycloalkyl, aryl, benzyl
also should cover salts of the amine

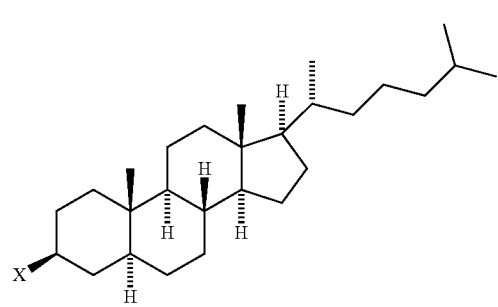

X = $NR_2$, NRCOR, $NHCONR_2$
OR, SR, OCOR, $OCONR_2$, $NHCNHNH_2$
R = H, alkyl, cycloalkyl, aryl, benzyl
also should cover salts of the amine

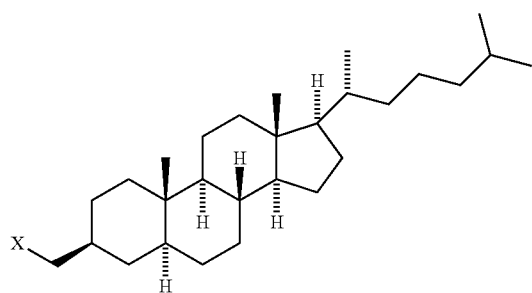

X = NR₂, NRCOR, NHCONR₂
OR, SR, OCOR, OCONR₂, NHCNHNH₂
R = H, alkyl, cycloalkyl, aryl, benzyl
also should cover salts of the amine

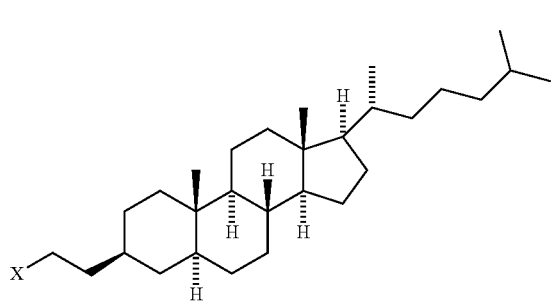

X = NR₂, NRCOR, NHCONR₂
OR, SR, OCOR, OCONR₂, NHCNHNH₂
R = H, alkyl, cycloalkyl, aryl, benzyl
also should cover salts of the amine

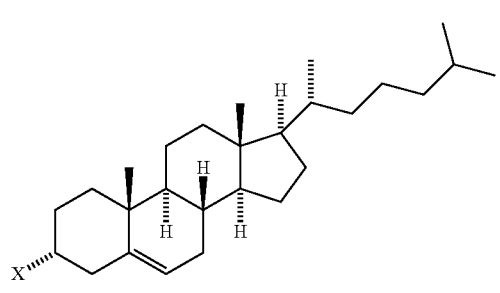

X = NR₂, NRCOR, NHCONR₂
OR, SR, OCOR, OCONR₂, NHCNHNH₂
R = H, alkyl, cycloalkyl, aryl, benzyl
also should cover salts of the amine

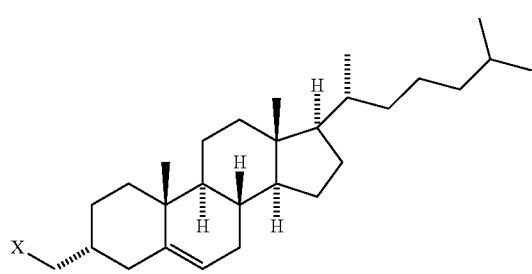

X = NR₂, NRCOR, NHCONR₂
OR, SR, OCOR, OCONR₂, NHCNHNH₂
R = H, alkyl, cycloalkyl, aryl, benzyl
also should cover salts of the amine

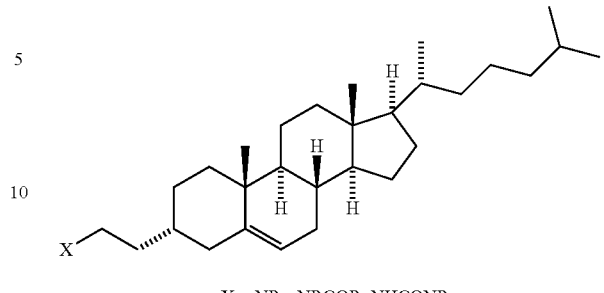

X = NR₂, NRCOR, NHCONR₂
OR, SR, OCOR, OCONR₂, NHCNHNH₂
R = H, alkyl, cycloalkyl, aryl, benzyl
also should cover salts of the amine

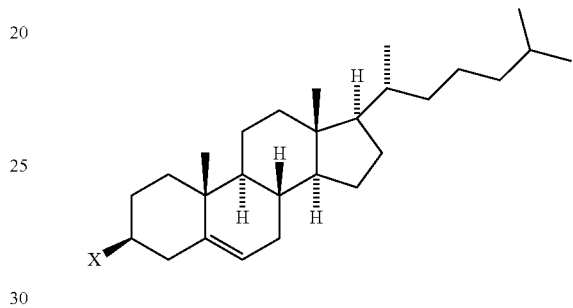

X = NR₂, NRCOR, NHCONR₂
OR, SR, OCOR, OCONR₂, NHCNHNH₂
R = H, alkyl, cycloalkyl, aryl, benzyl
also should cover salts of the amine

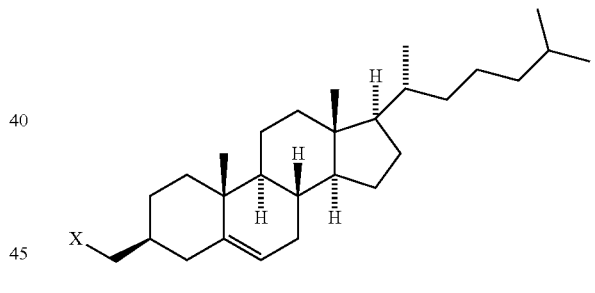

X = NR₂, NRCOR, NHCONR₂
OR, SR, OCOR, OCONR₂, NHCNHNH₂
R = H, alkyl, cycloalkyl, aryl, benzyl
also should cover salts of the amine

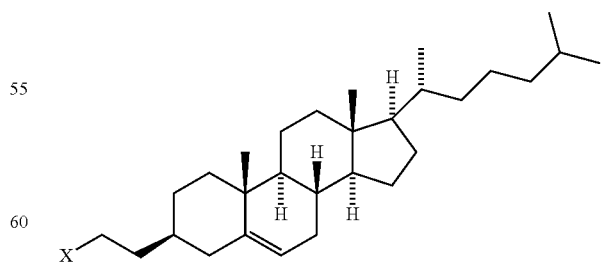

X = NR₂, NRCOR, NHCONR₂
OR, SR, OCOR, OCONR₂, NHCNHNH₂
R = H, alkyl, cycloalkyl, aryl, benzyl
also should cover salts of the amine

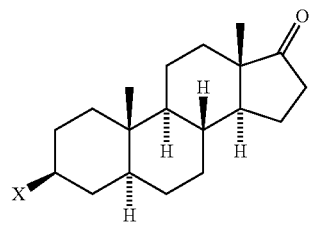

X = NR$_2$, NRCOR, NHCONR$_2$
OR, SR, OCOR, OCONR$_2$, NHCNHNH$_2$
R = H, alkyl, cycloalkyl, aryl, benzyl
also should cover salts of the amine

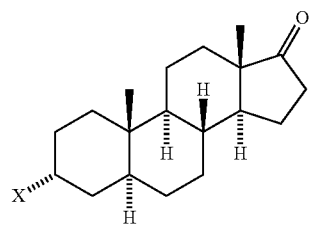

X = NR$_2$, NRCOR, NHCONR$_2$
OR, SR, OCOR, OCONR$_2$, NHCNHNH$_2$
R = H, alkyl, cycloalkyl, aryl, benzyl
also should cover salts of the amine

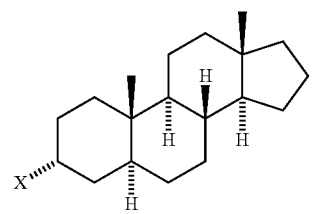

X = NR$_2$, NRCOR, NHCONR$_2$
OR, SR, OCOR, OCONR$_2$, NHCNHNH$_2$
R = H, alkyl, cycloalkyl, aryl, benzyl
also should cover salts of the amine

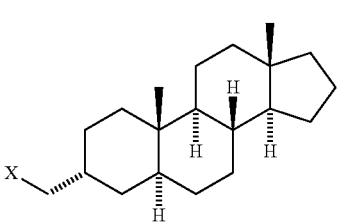

X = NR$_2$, NRCOR, NHCONR$_2$
OR, SR, OCOR, OCONR$_2$, NHCNHNH$_2$
R = H, alkyl, cycloalkyl, aryl, benzyl
also should cover salts of the amine

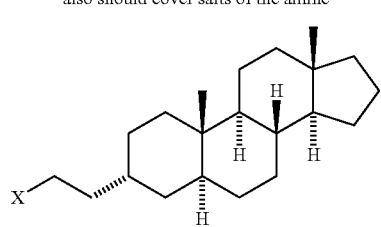

X = NR$_2$, NRCOR, NHCONR$_2$
OR, SR, OCOR, OCONR$_2$, NHCNHNH$_2$
R = H, alkyl, cycloalkyl, aryl, benzyl
also should cover salts of the amine

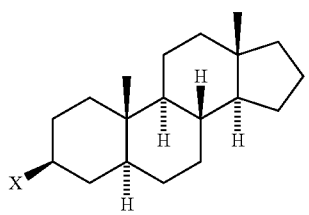

X = NR$_2$, NRCOR, NHCONR$_2$
OR, SR, OCOR, OCONR$_2$, NHCNHNH$_2$
R = H, alkyl, cycloalkyl, aryl, benzyl
also should cover salts of the amine

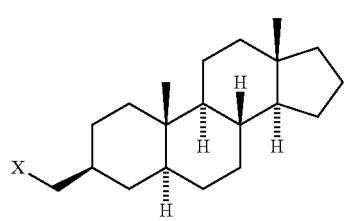

X = NR$_2$, NRCOR, NHCONR$_2$
OR, SR, OCOR, OCONR$_2$, NHCNHNH$_2$
R = H, alkyl, cycloalkyl, aryl, benzyl
also should cover salts of the amine

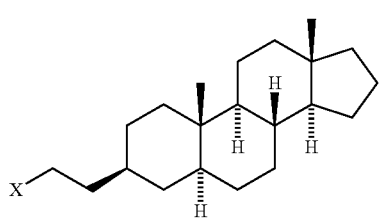

X = NR$_2$, NRCOR, NHCONR$_2$
OR, SR, OCOR, OCONR$_2$, NHCNHNH$_2$
R = H, alkyl, cycloalkyl, aryl, benzyl
also should cover salts of the amine

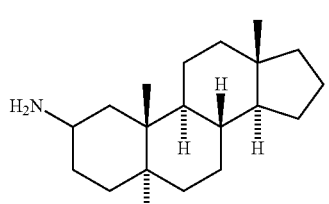

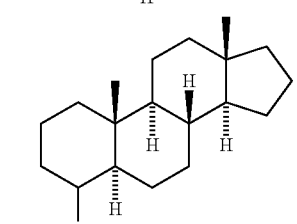

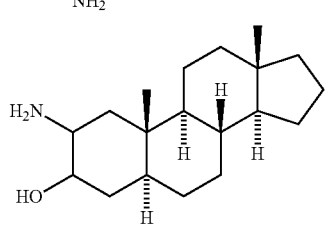

31
-continued
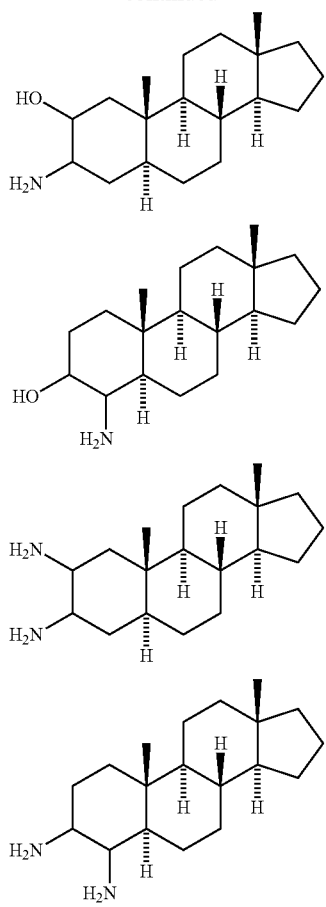
Example 5
Synthetic Schemes
Below are various schemes relating to analogs contemplated as being SHIP inhibitors of the present invention, as described below:
32
-continued
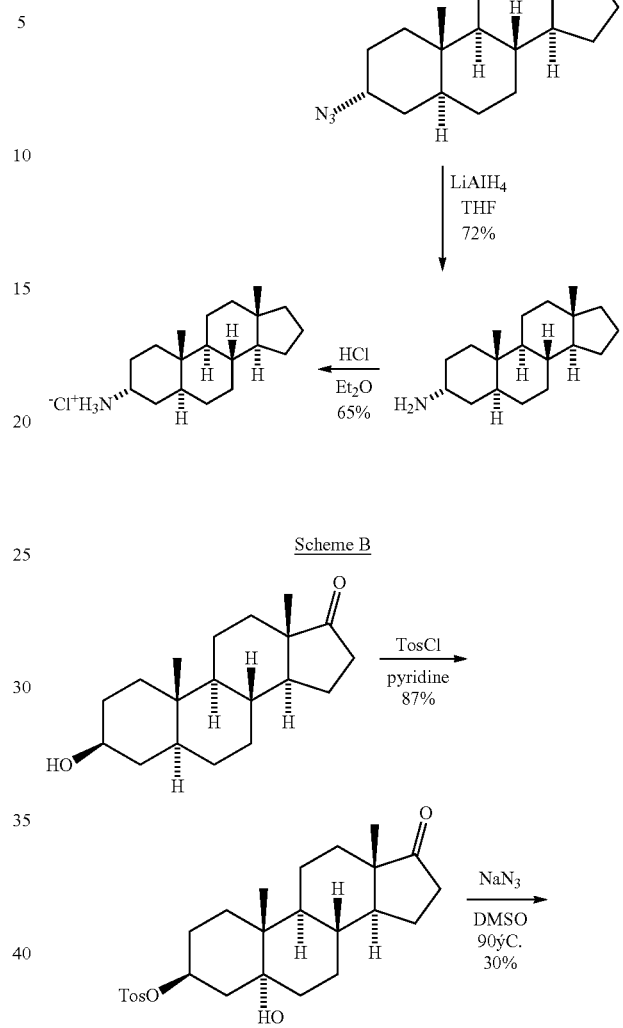
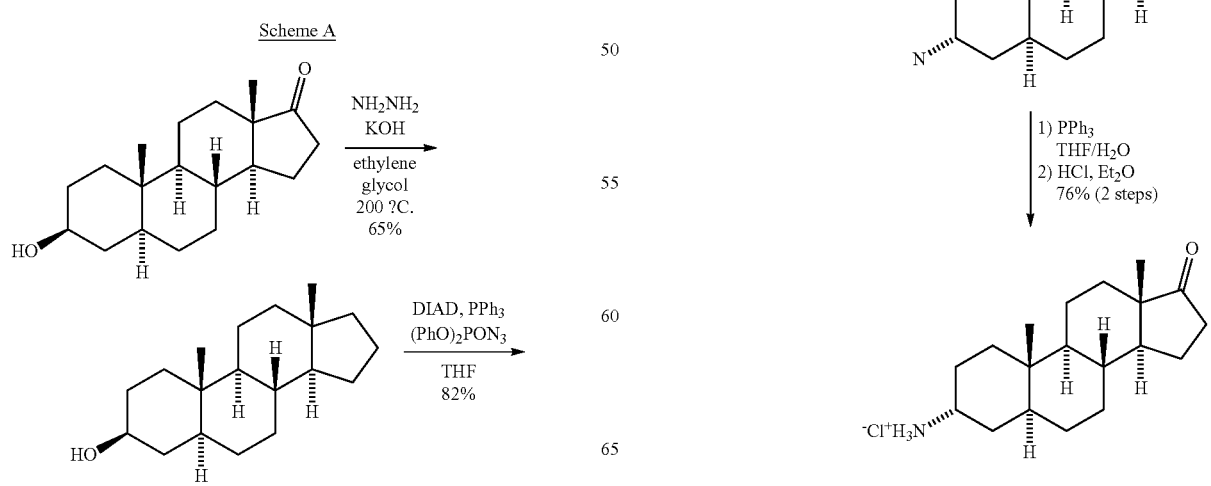

Scheme C

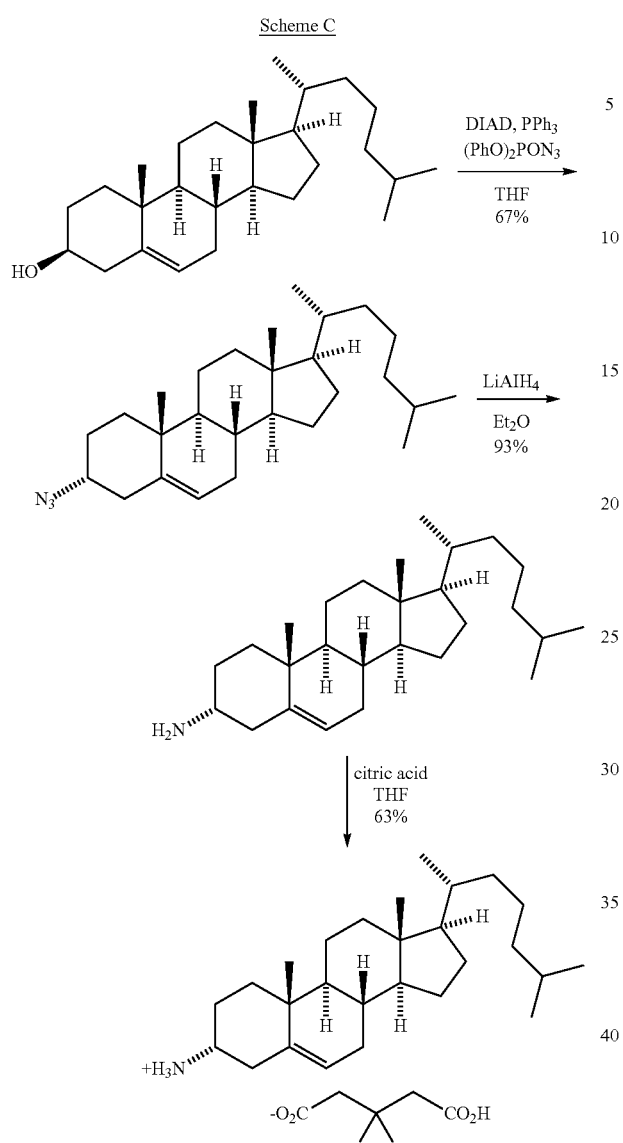

Example 6

5α-Androstan-3β-ol

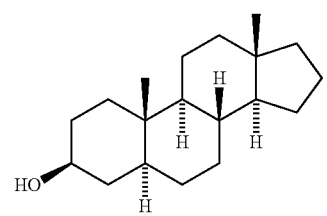

5α-Androstan-3β-ol: In a flame-dried flask, potassium hydroxide (1.58 g, 28.2 mmol) was dissolved in ethylene glycol (10 mL) by heating. The solution was cooled at room temperature before adding trans-androsterone (2.00 g, 6.89 mmol) and hydrazine hydrate (0.98 mL, 20.2 mmol). The solution was heated to reflux at 208° C. After 23 h, the solution was cooled at room temperature before adding HCl (14.1 mL, 2M). It was extracted with $CH_2Cl_2$ (4×30 mL). The organic layer were collected, combined, dried over $Na_2SO_4$, and concentrated under reduced pressure. The resulting solid residue was recrystallized in MeOH to afford 5α-androstan-3β-ol (1.56 g, 82%). $^1$H NMR (300 MHz, $CDCl_3$): d 3.58 (heptet, J=4.9 Hz, 1H), 1.76-1.82 (m, 1H), 1.70-1.75 (m, 2H), 1.65-1.69 (m, 2H), 1.61-1.63 (m, 1H), 1.57-1.60 (m, 1H), 1.52-1.57 (m, 2H), 1.47-1.50 (m, 1H), 1.40-1.45 (m, 1H), 1.33-1.39 (m, 1H), 1.29-1.30 (m, 1H), 1.22-1.28 (m, 4H), 1.04-1.17 (m, 4H), 0.9-1.02 (m, 1H), 0.85-0.93 (m, 2H), 0.80 (s, 3H), 0.68 (s, 3H) 0.60-0.65 (m, 1H).

Example 7

3α-Azido-5α-Androstane

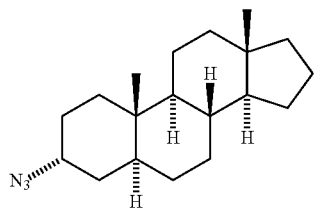

3α-Azido-5α-Androstane: In a 50 mL round bottom flask, 5α-androstan-3β-ol (1.12 g, 4.05 mmol) was dissolved in THF (20 mL). $PPh_3$ (1.06 g, 4.04 mmol) was added into the solution followed by DIAD (0.83 mL, 4.05 mmol). The resulting yellow solution was stirred continuously at room temperature for 10 min before adding $(PhO)_2PON_3$ (0.88 mL, 4.05 mmol). The solution was stirred continuously at room temperature. After 24 h, the reaction mixture was concentrated and the residue was recrystallized to afford 3α-azido-5α-androstane as a white solid (0.90 g, 74%). $^1$H NMR (300 MHz, $CDCl_3$): δ 3.88 (p, J=2.8 Hz, 1H), 1.71-1.72 (m, 1H), 1.67-1.70 (m, 3H), 1.59-1.64 (m, 2H), 1.57-1.53 (m, 3H), 1.45-1.52 (m, 3H), 1.36-1.42 (m, 2H), 1.26-1.31 (m, 1H), 1.18-1.24 (m, 3H), 1.14-1.17 (m, 2H), 1.13-1.10 (m, 1H), 0.85-1.03 (m, 2H), 0.79 (s, 3H), 0.72-0.77 (m, 1H), 0.69 (s, 3H).

Example 8

3α-Amino-5α-Androstane

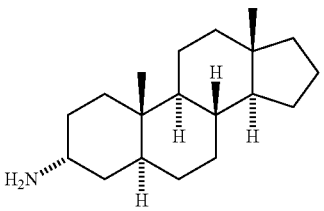

3α-Amino-5α-Androstane: In round bottom flask, $LiAlH_4$ (0.39 g, 9.83 mmol, 95%) was suspended in THF (10 mL). The suspension was cooled at 0° C. using ice/$H_2O$ bath before adding a solution of α-azide (0.90 g, 2.98 mmol) in THF (5 mL). The solution was warmed to room temperature and refluxed at 80° C. for 4 h. The reaction was cooled to room temperature before diluting the solution with THF (15 mL). The diluted reaction mixture was cooled at 0° C. and quenched using a Fieser method. The reaction mixture was stirred continuously until it turned into a milky white solution. The solution was then filtered through celite and washed with THF. The filtrate was dried over $Na_2SO_4$ and concentrated under reduced pressure to afford 3α-amino-5α-androstane (0.59 g, 72%). IR (KBr): 2926, 2855, 1472, 1378, 1124, 753 cm$^{-1}$. $^1$H NMR (300 MHz, CDCl$_3$): d 3.18 (broad, 1H), 1.71-1.73 (m, 2H), 1.65-1.69 (m, 3H), 1.61-1.63 (m, 1H), 1.59-1.60 (m, 1H), 1.55-1.57 (m, 2H), 1.50-1.53 (m, 1H), 1.40-1.45 (m, 3H), 1.30-1.32 (m, 1H), 1.23-1.29 (m, 3H), 1.18-1.21 (m, 3H), 1.14-1.18 (m, 2H), 1.07-1.10 (m, 2H), 0.89-1.99 (m, 2H), 0.78 (s, 3H), 0.69 (s, 3H).

Example 9

3α-Amino-5α-androstane hydrochloride

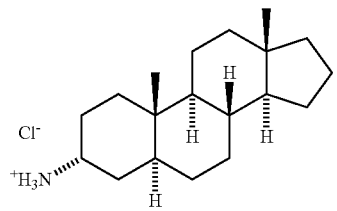

3α-Amino-5α-androstane hydrochloride: The α-amine 11 (0.20 g, 0.73 mmol) was dissolved in Et$_2$O (5 mL). A solution of HCl in Et$_2$O (0.73 mL, 2 M) was added dropwise which resulted to the formation of precipitate. The solution was filtered and the precipitate was collected, washed over Et$_2$O, and dried over vacuum to afford 3α-amino-5α-androstane hydrochloride (0.15 g, 65%) as a white solid. IR (KBr): 3320, 2945, 1619, 1495, 1443, 1379 cm$^{-1}$. $^1$H NMR (300 MHz, CDCl$_3$): d 8.45 (broad, 3H), 3.60 (broad, 1H), 1.84 (broad, 2H), 1.62-1.69 (m, 8H), 1.51-1.58 (m, 4H), 1.37-1.44 (m, 1H), 1.23-1.29 (m, 2H), 1.09-1.20 (m, 4H), 0.92-1.07 (m, 3H), 0.79 (s, 3H), 0.69 (s, 3H).

Example 10

3α-Acetamido-5α-Androstane

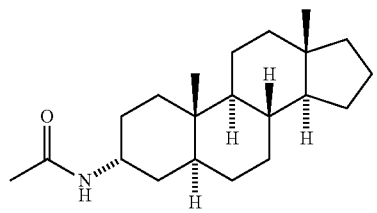

3α-Acetamido-5α-Androstane: The α-amine (0.20 g, 0.73 mmol) was dissolved THF (3 mL) in a round bottom flask. Et$_3$N (0.12 mL, 0.88 mmol) was added dropwise and the resulting solution was cooled at 0° C. Acetyl chloride (0.05 mL, 0.80 mmol) was added dropwise into the cooled solution which resulted on the formation of white precipitate. The milky white solution was stirred continuously for 15 min at 0° C. before allowing the reaction mixture to warm up to room temperature. THF (5 mL) was added and the diluted solution was washed with HCl (10 mL, 1 M), brine solution (10 mL), and H$_2$O (10 mL). The organic layer was collected, dried over Na$_2$SO$_4$, and concentrated under reduced pressure. Recrystallization of the solid residue using EtOH afforded 3α-acetamido-5α-androstane (0.05 g, 22%) as white solid. IR (KBr): 3264, 3077, 2933, 2834, 1637, 1558 cm$^{-1}$. $^1$H NMR (300 MHz, CDCl$_3$): δ 5.70 (broad, 1H), 4.12 (m, 1H), 1.99 (s, 3H), 1.72-1.76 (m, 1H), 1.68-1.71 (m, 2H), 1.62-1.66 (m, 2H), 1.60-1.62 (m, 2H), 1.56-1.58 (m, 1H), 1.52-1.55 (m, 1H), 1.48-1.51 (m, 1H), 1.42-1.46 (m, 1H), 1.36-1.39 (m, 1H), 1.29-1.34 (m, 2H), 1.23-1.27 (m, 1H), 1.21 (d, J=3.0 Hz, 1H), 1.18-1.19 (m, 1H), 1.12-1.17 (m, 2H), 1.08-1.11 (m, 1H), 1.00-1.06 (m, 1H), 0.92-0.97 (m, 1H), 0.84-0.90 (m, 1H), 0.81 (s, 3H), 0.71-0.77 (m, 1H), 0.69 (s, 3H).

Example 11

3β-Tosyloxy-5α-Androstan-17-one

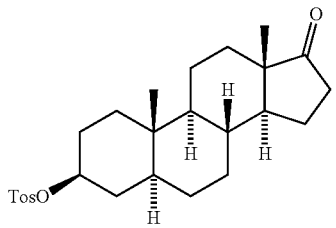

3β-Tosyloxy-5α-Androstan-17-one: In a 25 mL round bottom flask, trans-androsterone (1.00 g, 3.44 mmol) and p-toluenesulfonyl chloride (1.51 g, 7.91 mmol) was dissolved in in pyridine (4.30 mL). The reaction mixture was stirred continuously at room temperature. After 24 h, the reaction mixture was quenched by adding H$_2$O (10 mL) and it was extracted with CH$_2$Cl$_2$ (3×20 mL). All organic layers were collected, combined together and washed over HCl (3×20 mL, 2 M), brine solution (3×20 mL), and H$_2$O (3×20 mL), dried over Na$_2$SO$_4$, and concentrated under reduced pressure afforded 3β-tosyloxy-5α-androstan-17-one (1.33 g, 87%) as a white solid. $^1$H NMR (300 MHz, CDCl$_3$): d 7.79 (dt, J=8.3, 1.9 Hz, 2H), 7.33 (dd, J=8.0, 0.5 Hz, 2H), 4.42 (h, J=5.9 Hz, 1H), 2.44 (s, 3H), 2.38-2.47 (m, 1H), 1.99-2.11 (m, 1H), 1.86-1.95 (m, 1H), 1.78-1.80 (m, 1H), 1.71-1.77 (m, 2H), 1.65-1.69 (m, 1H), 1.56-1.64 (m, 3H), 1.44-1.55 (m, 3H), 1.30-1.31 (m, 1H), 1.28-1.29 (m, 2H), 1.22-1.24 (m, 1H), 1.18-1.20 (m, 1H), 1.04-1.16 (m, 1H), 0.85-1.00 (m, 2H), 0.84 (s, 3H), 0.80 (s, 1H), 0.60-0.69 (m, 1H).

Example 12

3α-Azido-5α-Androstan-17-one

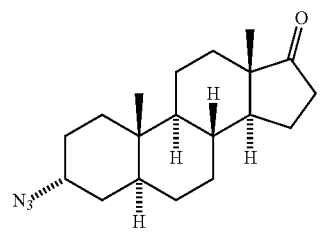

3α-Azido-5α-Androstan-17-one: A suspension of tosylate (1.33 g, 2.99 mmol) and NaN$_3$ (1.94 g, 29.9 mmol) in DMSO (75 mL) was heated to reflux at 90° C. After approximately 5 h, the reaction mixture was cooled at room temperature before adding H$_2$O (10 mL). The diluted solution was extracted with Et$_2$O (3×20 mL). All organic layers were collected, dried over MgSO$_4$, and concentrated under reduced pressure. The solid residue was recrystallized in EtOH to afford 3α-azido-5α-androstan-17-one (0.28 g, 30%). $^1$H NMR (300 MHz, CDCl$_3$): d 3.88 (pentet, J=2.6 Hz, 1H), 2.43 (dd, J=10.3, 9.6 Hz, 1H), 2.00-2.12 (m, 1H), 1.88-1.97 (m, 1H), 1.81-1.83 (m, 1H), 1.76-1.78 (m, 1H), 1.66-1.72 (m, 2H), 1.62-1.65 (m, 1H), 1.51-1.56 (m, 2H), 1.39-1.49 (m, 4H), 1.17-1.34 (m, 7H), 0.94-1.08 (m, 1H), 0.85 (s, 3H), 0.81 (s, 3H).

Example 13

3α-Amino-5α-androstan-17-one hydrochloride

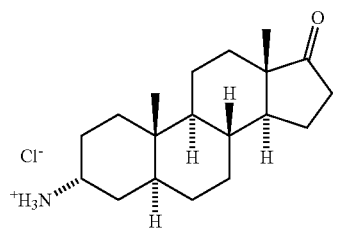

3α-Amino-5α-androstan-17-one hydrochloride: In a flame dried flask, azide (0.28 g, 0.89 mmol) and PPh$_3$ (0.36 g, 1.37 mmol) was dissolved in THF (15 mL). The solution was stirred continuously at room temperature for 18 h. H$_2$O (3 mL) was added and the solution was heated to reflux at 80° C. After 1 h, the solution was cooled at room temperature. The organic layer was collected, dried over Na$_2$SO$_4$, and concentrated under reduced pressure. The residue was dissolved Et$_2$O (7 mL) and a solution of HCl (0.89 mL, 2 M) was added which resulted to formation of precipitate. The precipitate was filtered over filter paper, washed over Et$_2$O, and dried to afford 3α-amino-5α-androstan-17-one hydrochloride (0.22 g, 76%) as white solid. IR (KBr): 3326, 2923, 1737, 1496, 1455, 731 cm$^{-1}$. $^1$H NMR (300 MHz, CDCl$_3$): δ 8.42 (broad, 3H), 3.61 (broad, 1H), 2.42 (dd, J=11.1, 8.7 Hz, 1H), 2.00-2.13 (m, 1H), 1.86-1.94 (m, 2H), 1.76-1.83 (m, 3H), 1.44-1.64 (m, 7H), 1.19-1.38 (m, 6H), 0.95-1.13 (m, 2H), 0.84 (s, 3H), 0.81 (s, 3H).

Example 14

3α-Azidocholest-5-ene

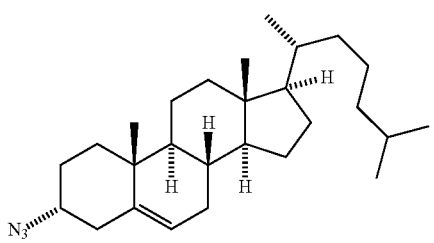

3α-Azidocholest-5-ene: Cholesterol (7.76 mmol, 3.0 g) and triphenylphosphine (7.76 mmol, 2.04 g) were dissolved in 77.6 mL of anhydrous tetrahydrofuran. Diisopropyl azodicarboxylate (7.76 mmol, 1.5 mL) was then added dropwise. After stirring the orange mixture for a few minutes, diphenylphosphoryl azide (7.76 mmol, 1.68 mL) was added dropwise. After 24 hours, the pale yellow reaction mixture was concentrated. Purification by silica gel chromatography (100% hexanes) afforded 3α-azidocholest-5-ene (2.14 g, 67%) as a white solid. mp 110-112° C.; TLC R$_f$=0.87 (20% ethyl acetate/hexanes); IR (thin film) 2946, 2914, 2845, 2083 cm$^{-1}$; $^1$H NMR (300 MHz, CDCl$_3$) δ 5.42-5.40 (m, 1H), 3.89 (t, 1H, J=2.9 Hz), 2.58-2.49 (m, 1H), 2.23-2.16 (m, 1H), 2.16-1.93 (m, 2H), 1.89-1.05 (m, 24H), 1.02 (s, 3H), 0.93 (d, 3H, J=6.5 Hz), 0.88 (d, 6H, J=6.6 Hz), 0.69 (s, 3H).

Example 15

3α-Aminocholest-5-ene

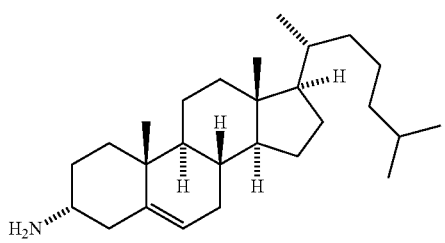

3α-Aminocholest-5-ene: 3α-Azidocholest-5-ene (4.62 mmol, 1.9 g) was dissolved in 154 mL of anhydrous diethyl ether. Lithium aluminum hydride (46.2 mmol, 1.75 g) was then added in one portion. After 30 hours, the reaction mixture was cooled to 0° C. 1.75 mL of deionized water was then added dropwise. After stirring for five minutes, 1.75 mL of 15% aqueous NaOH was added dropwise. After stirring for another five minutes, 5.25 mL of deionized water was added dropwise. The reaction was then stirred until all the salts turned white. Immediately afterwards, the reaction was filtered, dried (Na$_2$SO$_4$), and concentrated to afford 3α-Aminocholest-5-ene (1.57 g, 93%) as a white solid. mp 104-106° C.; IR (thin film) 3367, 3343, 2931, 1557 cm$^{-1}$; $^1$H NMR (300 MHz, CDCl$_3$) d 5.37-5.34 (m, 1H), 3.15 (t, 1H, J=3.2 Hz), 2.61-2.54 (m, 1H), 2.04-1.74 (m, 6H), 1.63-1.03 (m, 21H), 1.00 (s, 3H), 0.91 (d, 3H, J=6.5 Hz), 0.86 (d, 6H, J=6.6 Hz), 0.67 (s, 3H).

Example 16

3α-Aminocholest-5-ene Hydrochloride

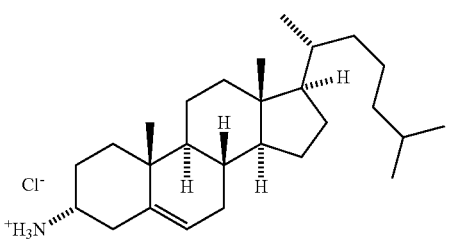

3α-Aminocholest-5-ene Hydrochloride: 3α-Aminocholest-5-ene (1.61 mmol, 0.59 g) was dissolved in 2 mL of anhydrous diethyl ether. Hydrogen chloride (2.0 M in diethyl ether) (3.22 mmol, 1.61 mL) was then added. After 3 hours, a white precipitate formed. The reaction was then filtered and the solid was washed with diethyl ether to afford 3α-aminocholest-5-ene hydrochloride (0.31 g, 46%) as a white solid. mp 293-295° C.; IR (thin film) 2947 cm$^{-1}$; $^1$H NMR (300 MHz, CDCl$_3$) d 8.25 (s, 3H), 5.52 (d, 1H, J=4.3 Hz), 3.58 (s, 1H), 2.61 (d, 1H, J=14.6 Hz), 2.36 (d, 1H, J=15.0 Hz), 2.02-1.07 (m, 26H), 1.01 (s, 3H), 0.91 (d, 3H, J=6.3 Hz), 0.86 (d, 6H, J=6.6 Hz), 0.67 (s, 3H).

Example 17

3α-Aminocholest-5-ene Citrate

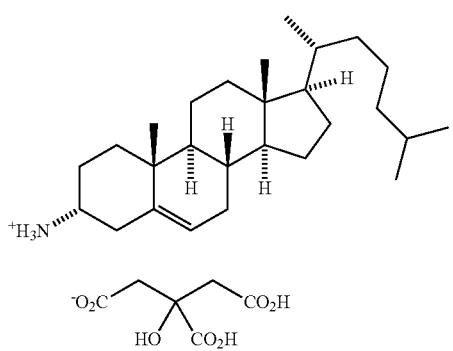

3α-Aminocholest-5-ene Citrate: 3α-Aminocholest-5-ene (0.82 mmol, 300 mg) was dissolved in 1.64 ml of tetrahydrofuran. Citric acid (0.82 mmol, 158 mg) was dissolved in 0.82 ml of tetrahydrofuran. The solution of citric acid was added dropwise to the solution of cholesterol amine. The mixture was stirred until the solution became very cloudy (approximately 15 minutes). The solution was vacuum filtered. The resulting white solid was washed with tetrahydofuran, collected, and dried under high vacuum for 12 hours to produce 298 mg of the 3α-aminocholest-5-ene citrate in 63% yield. mp: 172-174° C.; IR (thin film): 3469, 2954, 2247, 1714, 1591 cm$^{-1}$; $^1$H NMR (300 MHz, CD$_3$OD) δ: 5.53 (d, 1H, J=5.2 Hz), 3.55 (s, 1H), 2.84-2.70 (m, 4H), 2.80-2.70 (m, 1H), 2.19-1.0 (m, 28H), 1.07 (s, 3H), 0.95 (3H, J=6.5 Hz), 0.89 (d, 6H, J=6.6 Hz), 0.73 (s, 3H).

Example 18

Figure 6A:
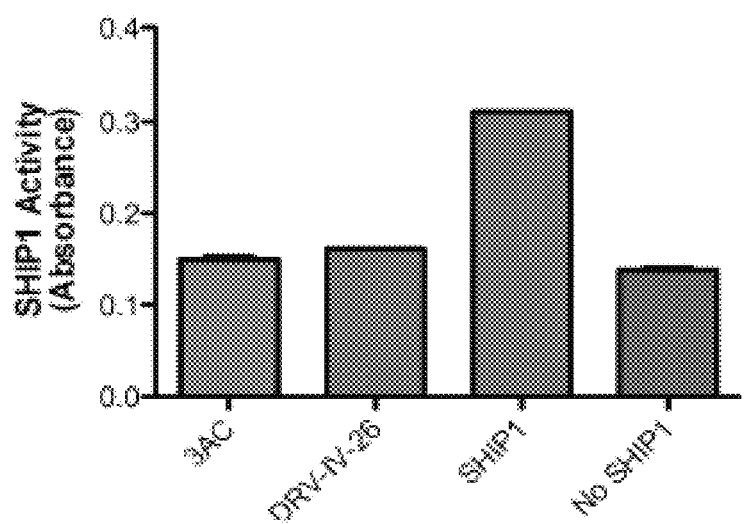
FIG. 6A, FIG. 6B, FIG. 6C, and FIG. 6D illustrate results relating to SHIP1 inhibitory activity of a 3AC derivative. As shown by the results, a more soluble 3AC derivative retains SHIP1 inhibitory activity in vitro and in vivo.
Figure 6B:
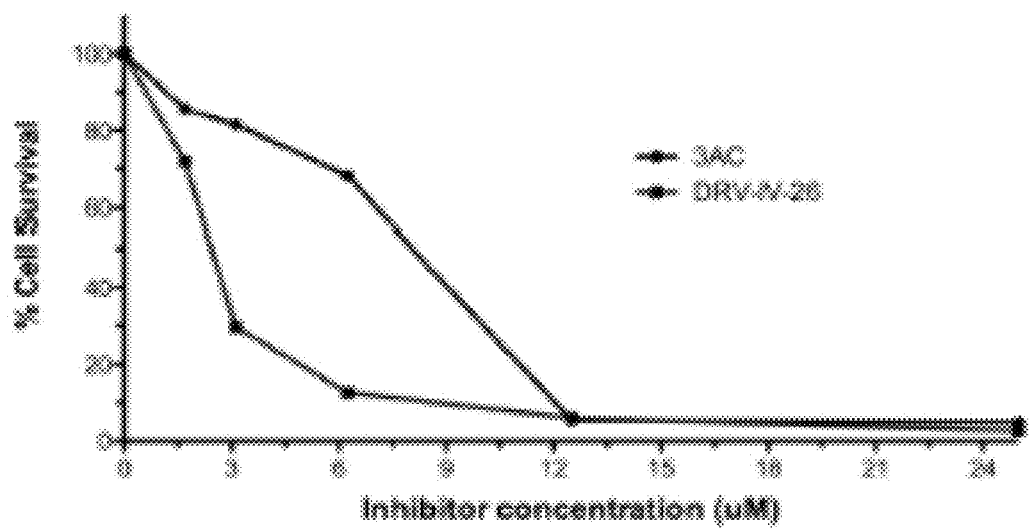
Figure 6C:
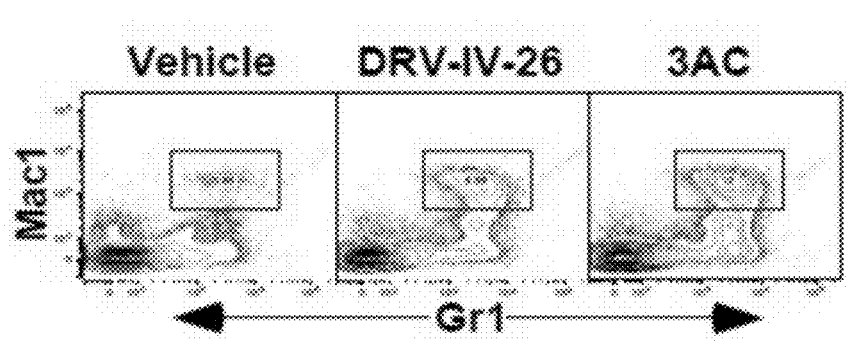
Figure 6D:
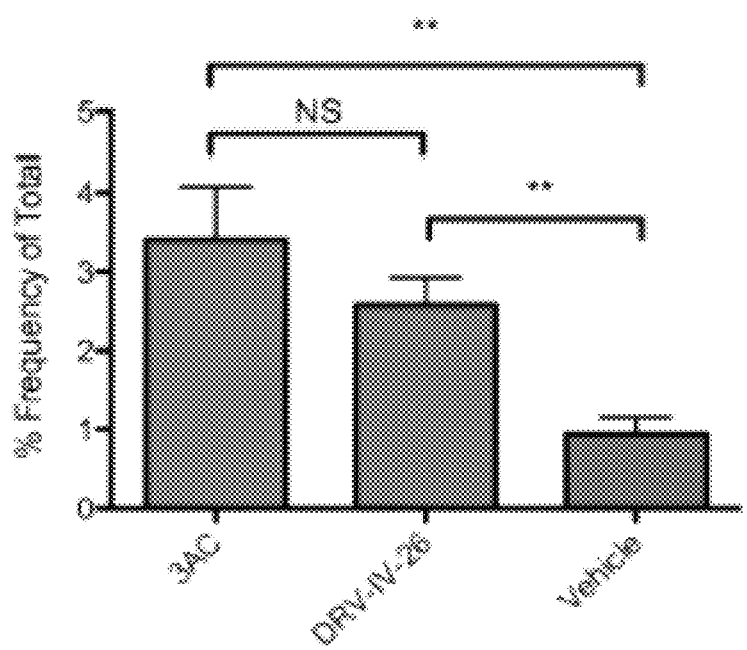

Synthesis and Identification of 3AC Derivatives with Increased Solubility and Potency The solubility of 3AC was assessed by calculating the distribution coefficient (CLogD). This calculation estimates the CLogD for 3AC at 7.17 indicating the molecule is very lipophilic. Thus, we have begun to develop novel 3AC analogs with increased aqueous solubility. One of these compounds, 3A5AS, has a CLogD of 3.33. Lipinski's rules (a common measure of small molecule pharmacokinetics) recommend a ClogD of <5 for in vivo applications. The chemical modifications made to derive 3A5AS have not altered its ability to inhibit SHIP1 as it retains equal inhibitory activity in vitro (FIG. 6A) and, surprisingly, it is more potent when used on intact cells, as it is substantially more cytotoxic for leukemia cells (FIG. 6B). 3A5AS is also more potent at inducing MIR cell numbers in vivo as it can induce a comparable MIR cell increase at 15 μM as opposed to 60 μM 3AC (FIG. 6C, D).

REFERENCES CITED

Citation of a reference herein shall not be construed as an admission that such reference is prior art to the present invention. All references cited herein are hereby incorporated by reference in their entirety. Below is a listing of references cited herein with reference number indicators:

1. Wang J W, et al. (2002) Influence of SHIP on the NK repertoire and allogeneic bone marrow transplantation. (Translated from eng) *Science* 295(5562):2094-2097 (in eng).
2. Ghansah T, et al. (2004) Expansion of myeloid suppressor cells in SHIP-deficient mice represses allogeneic T cell responses. (Translated from eng) *J Immunol* 173(12): 7324-7330 (in eng).
3. Wahle J A, et al. (2006) Cutting edge: dominance by an MHC-independent inhibitory receptor compromises NK killing of complex targets. (Translated from eng) *J Immunol* 176(12):7165-7169 (in eng).
4. Paraiso K H, Ghansah T, Costello A, Engelman R W, & Kerr W G (2007) Induced SHIP deficiency expands myeloid regulatory cells and abrogates graft-versus-host disease. (Translated from eng) *J Immunol* 178(5):2893-2900 (in eng).
5. Kerr W G (2008) A role for SHIP in stem cell biology and transplantation. *Curr Stem Cell Res Ther* 3(2):99-106.
6. Helgason C D, et al. (1998) Targeted disruption of SHIP leads to hemopoietic perturbations, lung pathology, and a shortened life span. *Genes & Development* 12(11):1610-1620.
7. Rauh M J, et al. (2005) SHIP represses the generation of alternatively activated macrophages. *Immunity* 23(4):361-374.
8. Takeshita S, et al. (2002) SHIP-deficient mice are severely osteoporotic due to increased numbers of hyper-resorptive osteoclasts. *Nat Med* 8(9):943-949.
9. Franke T F, Kaplan D R, Cantley L C, & Toker A (1997) Direct regulation of the Akt proto-oncogene product by phosphatidylinositol-3,4-bisphosphate [see comments]. *Science* 275(5300):665-668.
10. Jain S K, et al. (1996) PI 3-kinase activation in BCR/abl-transformed hematopoietic cells does not require interaction of p85 SH2 domains with p210 BCR/abl. (Translated from eng) *Blood* 88(5):1542-1550 (in eng).
11. Ivetac I, et al. (2009) Regulation of PI(3)K/Akt signalling and cellular transformation by inositol polyphosphate 4-phosphatase-1. (Translated from eng) *EMBO Rep* 10(5):487-493 (in eng).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A pharmaceutical composition selected from the group consisting of:

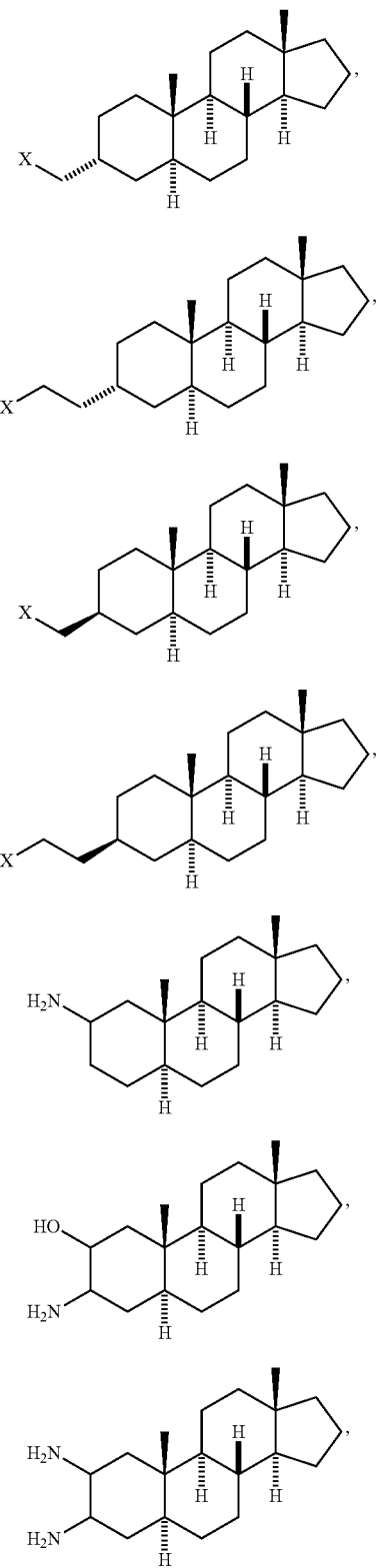

Formula 26,

Formula 27,

Formula 29,

Formula 30,

Formula 31,

Formula 34,

Formula 36, and a pharmaceutically acceptable salt thereof, wherein X, when present, is equal to $NR_2$, NRCOR, $NHCONR_2$, SR, OCOR, $OCONR_2$, or $NHCNHNH_2$, and wherein R, when present, is equal to H, alkyl, cycloalkyl, aryl, or benzyl.

2. A pharmaceutical composition comprising a SHIP inhibitor compound of formula (I), or a pharmaceutically acceptable salt thereof, wherein formula (I) is as follows:

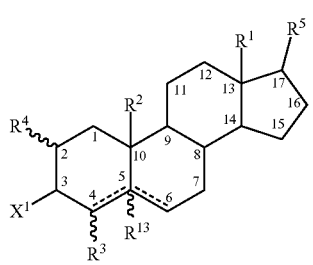

(I)

wherein
$R^1$ is methyl;
$R^2$ is methyl;
$R^3$ is hydrogen, hydroxyl, substituted amino, and aminoalkyl;
$R^4$ is hydrogen, hydroxy, substituted amino, unsubstituted amino, and aminoalkyl;
$R^5$ is hydrogen;
$R^{13}$ is hydrogen;
$X^1$ is selected from the group consisting of hydrogen, unsubstituted amino, and aminoalkyl; and
the dotted lines represent optional double bonds;
wherein, at least one of $R^3$, $R^4$, or $X^1$ is selected from unsubstituted amino, and aminoalkyl,
wherein if a double bond exists between the 4,5 or 5,6 positions, then $R^{13}$ is absent, and
wherein said pharmaceutical composition is suitable for use in a mammal,
with the proviso that $X^1$ cannot be unsubstituted amino when $R^4$ is hydrogen, wherein at least two of $R^3$, $R^4$ or $X^1$ are selected from unsubstituted amino, and aminoalkyl, or wherein $R^3$, $R^4$, and $X^1$ are selected from unsubstituted amino, and aminoalkyl.

3. The pharmaceutical composition of claim 1, wherein said mammal is a human.

4. The pharmaceutical composition of claim 2, wherein said mammal is a human.

5. A pharmaceutical composition comprising a SHIP inhibitor compound of formula (I), or a pharmaceutically acceptable salt thereof, wherein formula (I) is as follows:

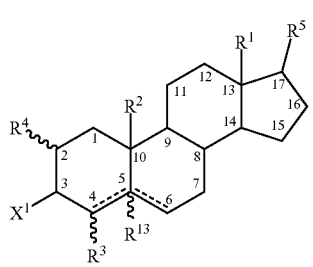

(I)

(I)

wherein
- $R^1$ is methyl;
- $R^2$ is methyl;
- $R^3$ is hydrogen, hydroxyl, substituted amino, or aminoalkyl;
- $R^4$ is selected from the group consisting of hydrogen, hydroxy, substituted amino, unsubstituted amino, and aminoalkyl;
- $R^5$ is hydrogen or alkyl;
- $R^{13}$ is hydrogen;
- $X^1$ is selected from the group consisting of hydrogen, unsubstituted amino, alkyl, and aminoalkyl; and
- the dotted lines represent optional double bonds;
- wherein at least two of $R^3$, $R^4$, or $X^1$ is selected from unsubstituted amino, and aminoalkyl; and
- wherein, if a double bond exists between the 4,5 or 5,6 positions, then $R^{13}$ is absent, and a pharmaceutically acceptable carrier.

6. The pharmaceutical composition of claim 1, wherein X is not present, and the SHIP inhibitor compound comprises the formula:

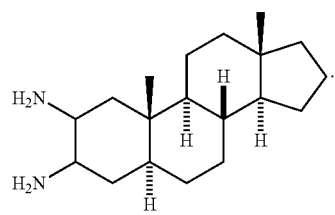

Formula 36

7. The pharmaceutical composition of claim 1, wherein X is not present, and the SHIP inhibitor compound comprises the formula:

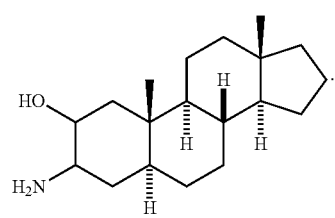

Formula 34

8. The pharmaceutical composition of claim 1, wherein X is not present, and the SHIP inhibitor compound comprises the formula:

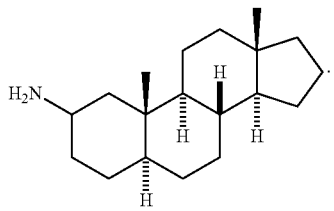

Formula 31

9. The pharmaceutical composition of claim 1, wherein X is not present, and the SHIP inhibitor compound consisting of the formula:

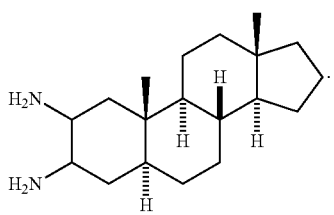

Formula 36

10. The pharmaceutical composition of claim 1, wherein X is not present, and the SHIP inhibitor compound consists of a pharmaceutically acceptable salt of the formula

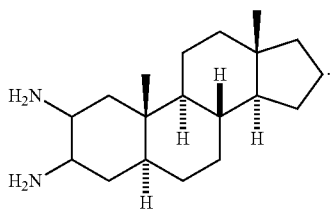

Formula 36

11. A pharmaceutical compound of formula:

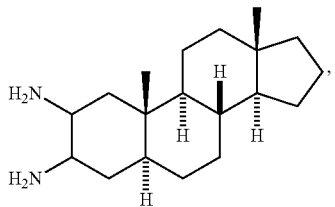

or a pharmaceutically acceptable salt thereof.

* * * * *